United States Patent
Abdolahad et al.

(10) Patent No.: US 11,047,824 B2
(45) Date of Patent: Jun. 29, 2021

(54) ELECTROCHEMICAL APPROACH FOR COVID-19 DETECTION

(71) Applicants: Mohammad Abdolahad, Tehran (IR); Zohreh Sadat Miripour, Tehran (IR); Hassan Sanati koloukhi, Tehran (IR); Fatemeh Zahra Shojaeian Zanjani, Tehran (IR); Hadi Ghafari, Tehran (IR); Naser Namdar Habashi, Tabriz (IR)

(72) Inventors: Mohammad Abdolahad, Tehran (IR); Zohreh Sadat Miripour, Tehran (IR); Hassan Sanati koloukhi, Tehran (IR); Fatemeh Zahra Shojaeian Zanjani, Tehran (IR); Hadi Ghafari, Tehran (IR); Naser Namdar Habashi, Tabriz (IR)

( * ) Notice: Subject to any disclaimer, the term of this patent is extended or adjusted under 35 U.S.C. 154(b) by 0 days.

(21) Appl. No.: 17/100,903

(22) Filed: Nov. 22, 2020

(65) Prior Publication Data
US 2021/0088469 A1 Mar. 25, 2021

Related U.S. Application Data

(60) Provisional application No. 63/013,001, filed on Apr. 21, 2020, provisional application No. 63/013,055, filed on Apr. 21, 2020.

(51) Int. Cl.
*G01N 27/327* (2006.01)
*G01N 33/487* (2006.01)

(52) U.S. Cl.
CPC ... *G01N 27/3275* (2013.01); *G01N 33/48771* (2013.01); *G01N 2800/26* (2013.01)

(58) Field of Classification Search
CPC ............ G01N 27/48; G01N 27/327; G01N 33/48714; G01N 2333/165;
(Continued)

(56) References Cited

PUBLICATIONS

Abdolahad et al. (Journal of Materials Science and Technology (32) (2016) 617-625.) (Year: 2016).*

* cited by examiner

*Primary Examiner* — Sally A Merkling
(74) *Attorney, Agent, or Firm* — Bajwa IP Law Firm; Haris Zaheer Bajwa

(57) ABSTRACT

A system for diagnosing COVID-19 infection. The system includes an electrochemical probe with three needle-shaped electrodes configured to be inserted into a sputum sample, an electrochemical stimulator-analyzer electrically connected to the electrochemical probe, a memory having processor-readable instructions stored therein, and a processor configured to access the memory and execute the processor-readable instructions to perform a method. The method includes applying a sweeping range of electrical potentials to the electrochemical probe utilizing the electrochemical stimulator-analyzer, measuring a set of generated electrical currents versus the applied sweeping range of electrical potential utilizing the electrochemical stimulator-analyzer, receiving the set of electrical currents from the electrochemical stimulator-analyzer, measuring a level of reactive oxygen species (ROS) in the sputum sample by measuring a current peak of the set of electrical currents, and detecting a COVID-19 infection status based on the measured level of ROS. Detecting the COVID-19 infection status includes detecting an infection with COVID-19 if the measured current peak is in a first range of current peaks and detecting a non-infection with COVID-19 if the measured current peak is in a second range of current peaks.

9 Claims, 11 Drawing Sheets

(58) Field of Classification Search
CPC ......... G01N 27/3275; G01N 33/48771; G01N 2800/26; A61B 10/0051
See application file for complete search history.

ELECTROCHEMICAL APPROACH FOR COVID-19 DETECTION

CROSS-REFERENCE TO RELATED APPLICATION

This application claims the benefit of priority from pending U.S. Provisional Patent Application Ser. No. 63/013,001 filed on Apr. 21, 2020, and entitled "AN ELECTROCHEMICAL APPROACH FOR COVID-19 DETECTION" and pending U.S. Provisional Patent Application Ser. No. 63/013,055 filed on Apr. 21, 2020, and entitled "REAL-TIME DIAGNOSIS OF COVID-19 IN FRESH SPUTUM BY ELECTROCHEMICAL TRACING OF VIRAL-INDUCED REACTIVE OXYGEN SPECIES (ROS) IN LUNG EPITHELIUM", which are both incorporated herein by reference in their entirety.

TECHNICAL FIELD

The present disclosure generally relates to detecting COVID-19 infection in a patient, and particularly, to an electrochemical approach to detect COVID-19 infection status of a patient by measuring reactive oxygen species (ROS) in fresh sputum.

BACKGROUND

COVID-19 has become one of the main health challenges of the world since February 2020. It is a shocking worldwide viral pandemic of which has affected the health, economy, communications, and all aspects of social activities all over the world. Its similar symptoms to SARS (which was discovered in 2003) such as respiratory syndromes convinced the scientist to name it SARS-CoV-2. But it is much more contagious than SARS-CoV-2. Based on reports of the World Health Organization (WHO), at least more than 7 million people had contacted this disease up to June 2020. Moreover, 400,000 people have died because of COVID-19 until June 2020. The non-controlled nature of this pandemic has forced researchers to develop new assays for early diagnosis or pre-screening to better diagnose and isolate individuals are suspected to be infected. Early diagnosis of this viral disease is very important since it can aid in preventing and reducing the mortality rate.

Hence, there is a need for a real-time, simple, cost-effective and precise method, system, and associated apparatus for fast reliable detection of COVID-19. Furthermore, there is a need for a fast-diagnosing and easy-to-use method to detect COVID-19 infection in a suspicious person to avoid further spreading the virus. Moreover, there is a need for a cost-effective and simple method to detect COVID-19 in suspicious people without any need for expensive and complicated chemical reagents.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary system for diagnosing COVID-19 infection. The system may include an electrochemical probe with three needle-shaped electrodes, an electrochemical stimulator-analyzer electrically connected to the electrochemical probe, and a processing unit electrically connected to the electrochemical stimulator-analyzer. The three needle-shaped electrodes may be configured to be inserted into a sputum sample. The processing unit may include a memory having processor-readable instructions stored therein, and a processor. The processor may be configured to access the memory and execute the processor-readable instructions. The processor may be configured to perform a method by executing the processor-readable instructions. The method may include applying a sweeping range of electrical potentials to the electrochemical probe utilizing the electrochemical stimulator-analyzer, measuring a set of generated electrical currents versus the applied sweeping range of electrical potential utilizing the electrochemical stimulator-analyzer, receiving the set of electrical currents from the electrochemical stimulator-analyzer, measuring a level of reactive oxygen species (ROS) in the sputum sample by measuring a current peak of the set of electrical currents, and detecting a COVID-19 infection status based on the measured level of ROS. In an exemplary implementation, detecting the COVID-19 infection status may include detecting an infection with COVID-19 if the measured current peak is in a first range of current peaks and detecting a non-infection with COVID-19 if the measured current peak is in a second range of current peaks.

In an exemplary embodiment, the first range of current peaks may include a range of current peaks of more than 230 µA. In an exemplary embodiment, the second range of current peaks may include a range of current peaks of less than 190 µA.

In an exemplary implementation, applying the sweeping range of electrical potentials to the electrochemical probe may include applying a sweeping range of electrical potentials from −0.8 V to +0.8 V with a scan rate of 100 mVs-1 to the electrochemical probe.

In an exemplary implementation, detecting the COVID-19 infection status may further include detecting a suspicious condition of COVID-19 infection if the measured current peak is in a third range of current peaks between the first range of current peaks and the second range of current peaks. In an exemplary embodiment, the suspicious condition of COVID-19 infection may include an indication that there is no definite determination regarding COVID-19 infection of the person. In an exemplary embodiment, the third range of current peaks may include a range of current peaks between 190 µA and 230 µA.

In an exemplary implementation, the method may further include generating a calibration data set. In an exemplary implementation, generating the calibration data set may include generating the first range of current peaks by measuring a first set of ROS values of a respective first set of sputum samples acquired from a plurality of persons infected with COVID-19 virus and generating the second range of current peaks by measuring a second set of ROS values of a respective second set of sputum samples acquired from a plurality of persons not infected with COVID-19 virus. In an exemplary implementation, detecting the COVID-19 infection status may further include comparing the measured the measured level of ROS with the ROS values in the calibration data set.

In an exemplary embodiment, the electrochemical probe may include a sensing head including the three needle-shaped electrodes. The three needle-shaped electrodes may be located at one end of the sensing head. In an exemplary embodiment, each of the three needle-shaped electrodes may include a steel needle including a conical tip and an array of multi-walled carbon nanotubes (MWCNTs) grown on the conical tip. In an exemplary embodiment, the three needle-shaped electrodes may be attached at the one end of the sensing head with a distance between 1 mm and 5 mm between each two respective needle-shaped electrodes placed next to each other.

In another general aspect, the present disclosure describes a method for diagnosing COVID-19 infection of a person. The method may include acquiring a sputum sample of a person, measuring a level of ROS in the sputum sample, and detecting a COVID-19 infection status of the person based on the measured level of ROS. In an exemplary implementation, measuring the level of ROS in the sputum sample may include recording a cyclic voltammetry (CV) pattern from the sputum sample and measuring a current peak of the recorded CV pattern. In an exemplary implementation, measuring the level of ROS in the sputum sample may include measuring the level of mitochondrial ROS induced by COVID-19 virus in respiratory epithelial host cells of the person.

In an exemplary implementation, detecting the COVID-19 infection status of the person based on the measured level of ROS may include detecting COVID-19 infection of the person if the measured current peak is in a first range of current peaks and detecting COVID-19 non-infection of the person if the measured current peak is in a second range of current peaks. In an exemplary embodiment, the first range of current peaks may include a range of current peaks of more than 230 µA. In an exemplary embodiment, the second range of current peaks may include a range of current peaks of less than 190 µA.

In an exemplary implementation, detecting the COVID-19 infection status of the person may further include detecting a suspicious condition of COVID-19 infection of the person if the measured current peak is in a third range of current peaks. The suspicious condition of COVID-19 infection of the person may include an indication that there is no definite determination regarding COVID-19 infection of the person. In an exemplary embodiment, the third range of current peaks may include a range of current peaks between 190 µA and 230 µA. In such implementations, the method may further include suggest/advise the person to stay in quarantine or social isolation over a time period between 1 day and 4 days and repeating steps of the exemplary method, including acquiring the sputum sample of the person, measuring the level of ROS in the sputum sample, and detecting the COVID-19 infection status of the person based on the measured level of ROS.

In an exemplary implementation, the method may further include generating a calibration data set. In an exemplary implementation, detecting the COVID-19 infection status of the person may further include looking up the measured current peak in the calibration data set by comparing the measured current peak with current peak values in the calibration data set.

In an exemplary implementation, generating the calibration data set may include generating the first range of current peaks and generating the second range of current peaks. In an exemplary implementation, generating the first range of current peaks may include recording a first set of CV patterns from a plurality of persons infected with COVID-19 virus and measuring a first set of current peaks of the respective first set of CV patterns. In an exemplary implementation, generating the second range of current peaks may include recording a second set of CV patterns from a plurality of persons not infected with COVID-19 virus and measuring a second set of current peaks of the respective second set of CV patterns.

In an exemplary implementation, acquiring the sputum sample of the person may include allowing the person to enter a sampling cabin, putting a fresh sputum into a sampling container by the person, and handing over the fresh sputum to an individual in a testing room located next to the sampling cabin. In an exemplary embodiment, the sampling cabin may be configured to isolate the person in a closed area, and apply a set of controlled conditions while acquiring the sputum sample. In an exemplary implementation, handing over the fresh sputum to the individual in the testing room may include transferring the fresh sputum from the sampling cabin to the testing room by the person utilizing an interface drawer, which may be movable between the sampling cabin and the testing room. In an exemplary implementation, acquiring the sputum sample of the person may include taking a bronchoalveolar lavage (BAL) fluid from a hospitalized patient.

In an exemplary implementation, applying the set of controlled conditions to the sampling cabin may include spraying a disinfectant agent into the sampling cabin and displacing air through the sampling cabin. In an exemplary implementation, displacing air through the sampling cabin may include flowing air inside the sampling cabin from a bottom side of the sampling cabin using a high-pressure air blower fan and flowing air outside the sampling cabin using an air suction fan placed above the sampling cabin.

In an exemplary implementation, recording the CV pattern from the sputum sample may include attaching a sensing head of an electrochemical probe to a handle of the electrochemical probe, where the sensing head may include three needle-shaped electrodes which may be located at one end of the sensing head. Recording the CV pattern from the sputum sample may further include connecting the handle of the electrochemical probe to an electrochemical stimulator-analyzer device, inserting the three needle-shaped electrodes into the sputum sample, applying a sweeping range of electrical potential from −0.8 V to +0.8 V with a scan rate of 100 mVs-1 to the electrochemical probe utilizing the electrochemical stimulator-analyzer device, and recording the CV pattern including a set of electrical currents versus the applied swept range of electrical potential.

In an exemplary embodiment, each of the three needle-shaped electrodes may include a steel needle comprising a conical tip and an array of multi-walled carbon nanotubes (MWCNTs) grown on the conical tip. In an exemplary embodiment, the three needle-shaped electrodes may be attached at the one end of the sensing head with a distance between 1 mm and 5 mm between each two respective needle-shaped electrodes placed next to each other.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
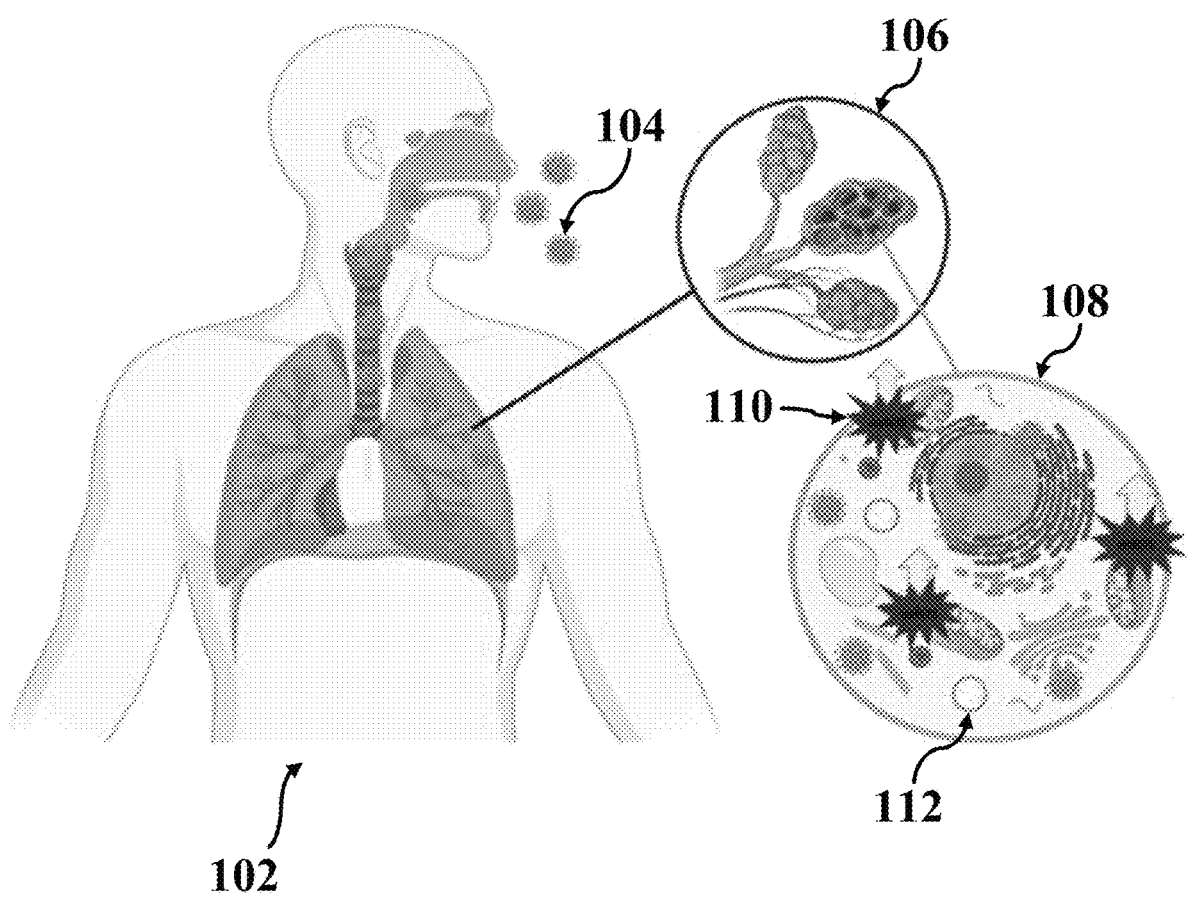
FIG. 1 illustrates a schematic view of the COVID viruses' effect in lung host cells by inducing mitochondrial reactive oxygen species (ROS) overproduction to promote viral replications, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

One of the crucial side effects of COVID viruses in lung host cells is inducing mitochondrial reactive oxygen species (ROS) functions to promote viral replications. In an exemplary embodiment, this occurs because mitochondrial reactive oxygen species are important for SARS-CoV 3a-induced NLRP3 inflammasome activation.

Dysregulation of inflammatory cytokines may lead to lung injury and pathogenesis of SARS-COV in a respiratory system with the underlying molecular mechanisms. Specifically, nod-like receptor family and pyrin domain-containing 3 (NLRP3) may be activated by virus infection and ROS may be released from damaged mitochondria due to a significant relation between far activation of the NLRP3 inflammasome and ROS generation. In other words, COVID-19 virus may stimulate ROS production in mitochondria of host respiratory cells to enhance its replication infection. Subsequently, intracellular pathway (i.e., NLRP3 activation), which may be activated against virus replication, may stimulate mitochondrial ROS production against viral disease. Then, cytokine storm may recall immunocells to accumulate in lung and respiratory system and attack the epithelium of lung/respiratory system by producing additive ROS. An exemplary approach for this phenomenon may entail that mitophagy/autophagy blockade results in the accumulation of damaged, ROS-generating mitochondria, which may activate NLRP3 inflammasome. Hence, all known NLRP3 activators generate ROS which may result in secretion of IL-1β in an NLRP3-ASC-caspase-1-dependent manner in THP-1 human macrophages to fight against a viral disease.

One of the most important secreted samples that might contain plenty of viral infected lung epithelium is fresh sputum. Herein, an exemplary real-time electrochemical diagnostic system and method is disclosed, which may include a diagnostic mechanism based on early traces of mitochondrial ROS overproduction as lung cells' dysfunctions induced by the COVID-19 virus regarding functional similarities between COVID-19 and COVID-2 in inducing acute respiratory syndrome. FIG. 1 shows a schematic view of the effect of COVID-19 virus 104 in lung host cells 108 by inducing overproduction of mitochondrial ROS 110 to promote viral replications, consistent with one or more exemplary embodiments of the present disclosure. ROS levels in sputum of person 102, who may be infected with COVID-19 virus 104, may be increased due to an overproduction of mitochondrial ROS 110 released from mitochondria 112. This overproduction of mitochondrial ROS 110 may be induced by COVID-19 virus 104 in respiratory epithelial host cells 108 via a three-step process. The exemplary process may include an increase in mitochondrial ROS 110 production to help virus infection, activation of NLRP3 inflammasome as well as an over increasing of mitochondrial ROS 110 production against virus replication, and cytokine storm which may recall immunocells in respiratory system and produce mitochondrial ROS 110 which may perturb lung and respiratory system functions. Respiratory epithelial host cells 108 may be detached from an exemplary alveoli 106, which may be affected by COVID-19 virus 104, and may be present in sputum sample of person 102. Hence, ROS levels in sputum are used herein as a criterion for screening people candidates for COVID-19 and detecting infected persons, and the exemplary method described herein may be based on electrochemical recording of ROS released from viral-infected lung epithelium.

The exemplary method and system disclosed here may be utilized to detect the ROS levels in sputum of candidates for COVID-19 who also may have some other respiratory disease such as asthma or cystic fibrosis; thereby, allowing for detecting COVID-19-infected asymptotic people especially in warm seasons even if their disease had not been detected by other assays. Although some ROS detection techniques and sensors such as spectroscopic methods, fluorescent-dependent methods, chemiluminescent probes, etc. were developed, none of them can be applied for in-vivo ROS detection induced by virus. Those methods and sensors may not be capable of precise and fast detection of ROS in a cost-effective manner due to their low specificity, sensitivity, and selectivity. Moreover, those methods and sensors may not be simply applicable due to their complexities.

FIG. 2A shows exemplary method 200 for diagnosing COVID-19 infection of a person, consistent with one or more exemplary embodiments of the present disclosure. Exemplary method 200 may include acquiring a sputum sample of a person (step 202), measuring a level of ROS in the sputum sample (step 204), and detecting a COVID-19 infection status of the person based on the measured level of ROS (step 206).

In detail, step 202 may include acquiring a sputum sample of a person. Acquiring a sputum sample of a person may comprise taking a sputum sample from the person at a particular location or retrieving a pre-taken sputum sample from the person. In an exemplary implementation, step 202 may further include putting the sputum sample acquired from the person in a sampling container. In an exemplary embodiment, the sampling container may include at least one of a vial, a Falcon, a vessel, etc. In an exemplary implementation, acquiring the sputum sample of the person (step 202) may include taking a bronchoalveolar lavage (BAL) fluid from a hospitalized patient. In an exemplary embodiment, the hospitalized patient may be a patient who may be hospitalized in an intensive care unit (ICU).

In an exemplary implementation, acquiring the sputum sample of the person (step 202) may be carried out in an isolation booth. FIG. 3 shows a schematic view of an exemplary isolation booth 300 for acquiring the sputum sample of person 302 (step 202), consistent with one or more exemplary embodiments of the present disclosure. In an exemplary implementation, acquiring the sputum sample of person 302 (step 202) may include allowing person 302 to enter sampling cabin 304, putting a fresh sputum into sampling container 308 by person 302, and handing over sampling container 308 containing the fresh sputum to an individual (e.g. a laboratory expert) in testing room 310 located next to the sampling cabin 304. In an exemplary embodiment, person 302 may be an asymptotic person with a COVID-19 infection.

In an exemplary implementation, sampling cabin 304 may be configured to isolate person 302 in a closed area, and apply a set of controlled conditions while acquiring the sputum sample. In an exemplary implementation, applying the set of controlled conditions to sampling cabin 304 may include spraying a disinfectant agent into sampling cabin 304, and displacing air through sampling cabin 304. In an exemplary implementation, the disinfectant agent may be sprayed utilizing sprayer 312 into sampling cabin 304. Exemplary sprayer 312 may be located above the sampling cabin 304.

In an exemplary implementation, displacing air through sampling cabin 304 may include flowing air inside sampling cabin 304 from a bottom side 314 of sampling cabin 304 using high-pressure air blower fan 316 and flowing air outside sampling cabin 304 using air suction fan 318, which may be placed above sampling cabin 304.

In an exemplary implementation, handing over sampling container 308 containing the fresh sputum to the individual in testing room 310 may include transferring sampling container 308 containing the fresh sputum from sampling cabin 304 to testing room 310 by person 302 utilizing interface drawer 306. In an exemplary embodiment, interface drawer 306 may be movable between sampling cabin 304 and testing room 310.

In an exemplary embodiment, the sputum sample may include fresh sputum that may be acquired of person 302. In an exemplary embodiment, volume of the sputum sample may be about 500 μl or less. In an exemplary embodiment, the sputum sample may include a mixture of the fresh sputum and an amount of water. The amount of water may be added to the fresh sputum; allowing for facilitation of step 204, which may include measuring a level of ROS in the sputum sample.

Furthermore, steps 204 and 206 respectively may include measuring a level of ROS in the sputum sample (step 204) and detecting a COVID-19 infection status of the person based on the measured level of ROS (step 206). In an exemplary implementation, an exemplary system may be prepared for carrying out measurement of the level of ROS in the sputum sample (step 204) and detecting the COVID-19 infection status of person 302 based on the measured level of ROS (step 206). FIG. 4A shows a schematic view of an exemplary system 400 for detecting COVID-19 infection based on measuring ROS level of a sputum sample, consistent with one or more exemplary embodiments of the present disclosure. In an exemplary implementation, system 400 may include an electrochemical probe 402, an electrochemical stimulator analyzer device 404, and a processing unit 406. Exemplary electrochemical probe 402 may be electrically connected to electrochemical stimulator analyzer device 404 via an electrical wire/cable or a wireless connection, and electrochemical stimulator analyzer device 404 may be electrically connected to processing unit 406 via electrical wires or a wireless connection. In an exemplary embodiment, the wireless connection may include Bluetooth devices or Bluetooth modules, which may be embedded in electrochemical probe 402, electrochemical stimulator analyzer device 404, and processing unit 406. The wireless connection may allow for simplifying utilizing parts of system 400 in arbitrary distances from each other. In an exemplary embodiment, a first end 420 of handle 410 may be electrically connected to the electrochemical stimulator-analyzer 404, for example via electrical wire 422.

In an exemplary embodiment, probe 402 may include sensing head 408 and handle 410. In an exemplary embodiment, sensing head 408 may include three needle-shaped electrodes 412, 414, and 416 located at one end 418 of sensing head 408. In an exemplary embodiment, three needle-shaped electrodes 412, 414, and 416 may include working electrode 412, counter electrode 414, and reference electrode 416, which may be configured to conduct electrochemical measurements. In an exemplary implementation, three needle-shaped electrodes 412, 414, and 416 may be configured to be inserted into exemplary sputum sample 432 acquired from person 302.

In an exemplary embodiment, each needle-shaped electrode of three needle-shaped electrodes 412, 414, and 416 may include a biocompatible conductive needle with a diameter between about 100 μm and about 1000 μm (1 mm) and a length between about 0.1 cm and about 1 cm. In an exemplary embodiment, each needle-shaped electrode of three needle-shaped electrodes 412, 414, and 416 may include a biocompatible metallic needle, for example, a steel needle. In one example, each needle-shaped electrode of three needle-shaped electrodes 412, 414, and 416 may include an acupuncture needle.

In an exemplary embodiment, each needle-shaped electrode of three needle-shaped electrodes 412, 414, and 416 may include an exemplary conical tip 440 and an exemplary array 442 of multi-walled carbon nanotubes (MWCNTs) that may be grown on conical tip 440. In an exemplary embodiment, exemplary conical tip 440 may include exemplary sharp point 444 with a diameter of less than about 50 μm. In an exemplary embodiment, each needle-shaped electrode of three needle-shaped electrodes 412, 414, and 416 may include a biocompatible conductive needle with an exemplary diameter of about 500 μm with sharp point 444 with an exemplary diameter of about 25 μm. In an exemplary embodiment, three needle-shaped electrodes 412, 414, and 416 may be attached at the one end 418 of sensing head 408 with a triangular distance between about 1 mm and about 5 mm from each other.

In an exemplary embodiment, array 442 of MWCNTs may include an array of vertically aligned multi-walled carbon nanotubes (VAMWCNTs). In an exemplary embodiment, array 442 of MWCNTs may include MWCNTs with a length of between about 0.5 μm and about 10 μm and a diameter of between about 20 nm and about 100 nm.

In an exemplary implementation, three needle-shaped electrodes 412, 414, and 416 may be sterilized before each ROS measurement according to step 204 regarding a requirement of utilizing clean and sterile three needle-shaped electrodes 412, 414, and 416, which may be in contact with the sputum sample in step 204. In another exemplary implementation, sensing head 408 may be changeable/replaceable with a new/fresh sensing head 408 regarding the requirement of utilizing clean and sterile three needle-shaped electrodes 412, 414, and 416. FIG. 4B shows a schematic view of an exemplary scenario in which sensing head 408 has been separated from handle 410 of exemplary electrochemical probe 402, consistent with one or more exemplary embodiments of the present disclosure. For each ROS measurement according to step 204, an old sensing head 408 may be separated from handle 410 and a new sensing head 408 may be attached to a second end 424 of handle 410.

Figure 2A:
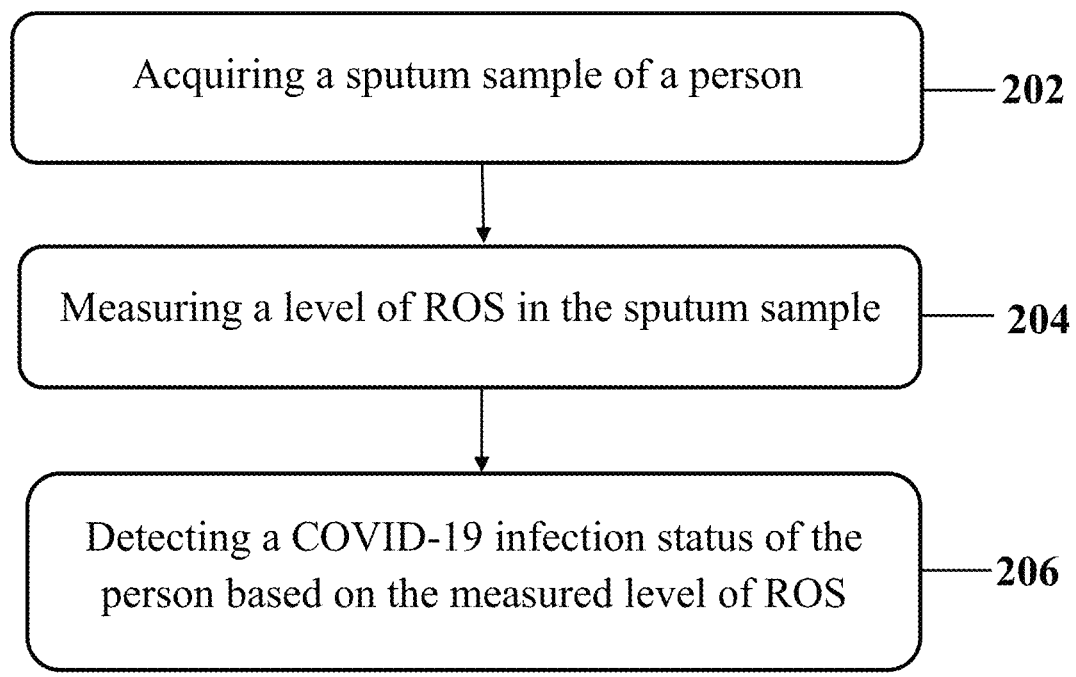
FIG. 2A illustrates an exemplary method for diagnosing COVID-19 infection of a person, consistent with one or more exemplary embodiments of the present disclosure.
Figure 4A:
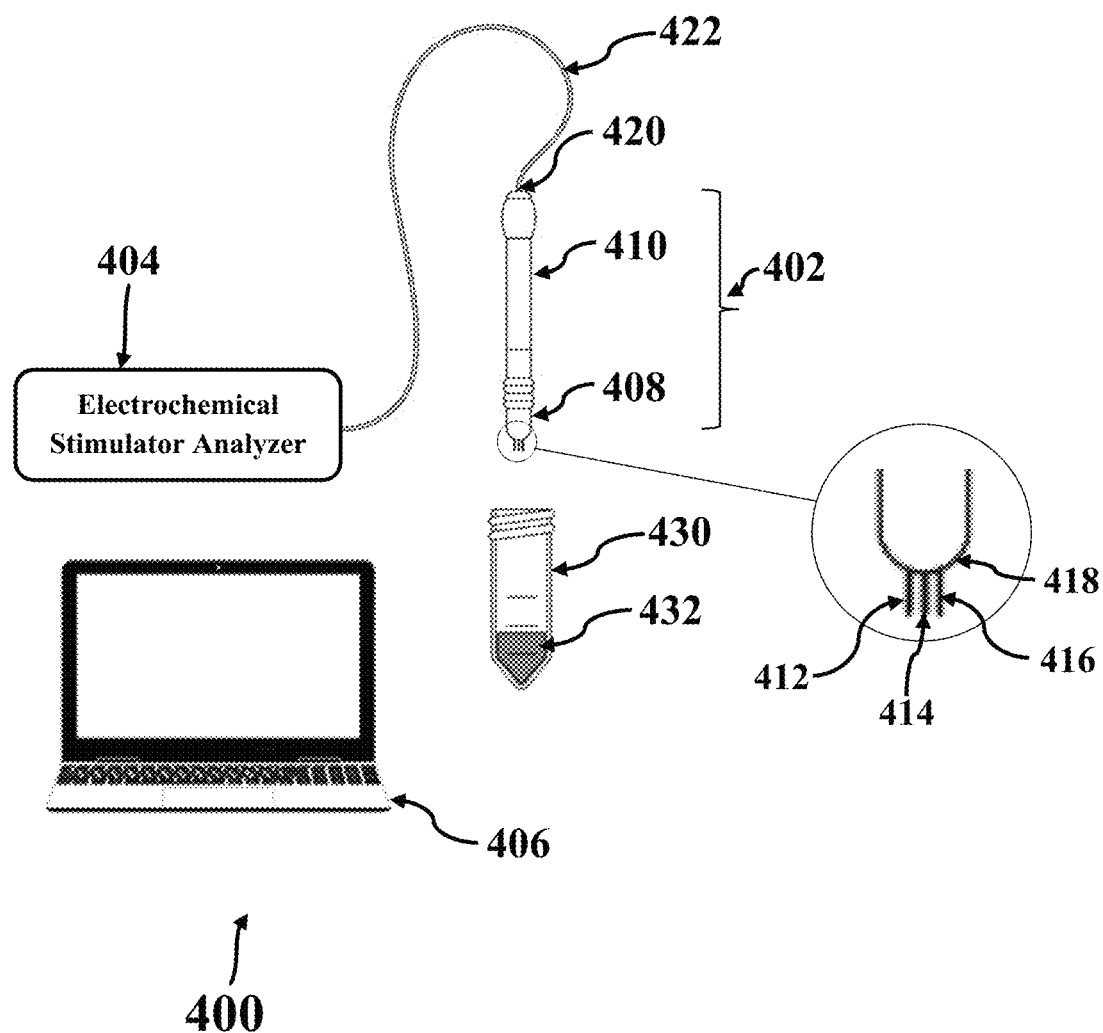
FIG. 4A illustrates a schematic view of an exemplary system for detecting COVID-19 infection based on measuring mitochondrial ROS level of a sputum sample, consistent with one or more exemplary embodiments of the present disclosure.
Figure 4B:
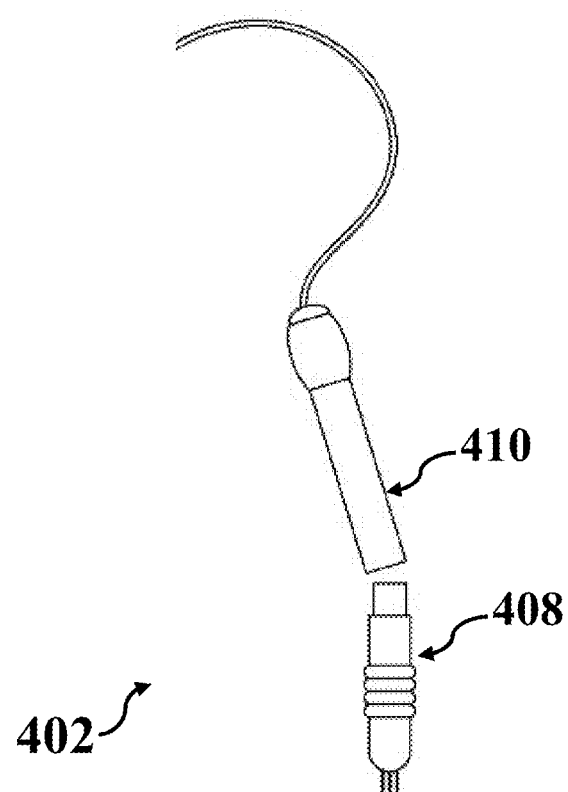
FIG. 4B illustrates a schematic view of an exemplary scenario in which an exemplary sensing head has been separated from an exemplary handle of the exemplary electrochemical probe, consistent with one or more exemplary embodiments of the present disclosure.

Regarding FIG. 2A with reference to FIG. 4A, step 204 may include measuring the level of ROS in exemplary sputum sample 432 in sampling container 430. In an exemplary implementation, measuring the level of ROS in sputum sample 432 (step 204) may include measuring the level of mitochondrial ROS, which may be induced by COVID-19 virus in respiratory epithelial host cells of person 302. A presence of COVID-19 virus in respiratory epithelial host cells of person 302 may lead to an increase in production of mitochondrial ROS by NLRP3 in mitochondria against viral replication and by immunocells accumulated in lung through a viral induced cytokine storm.

Figure 4C:
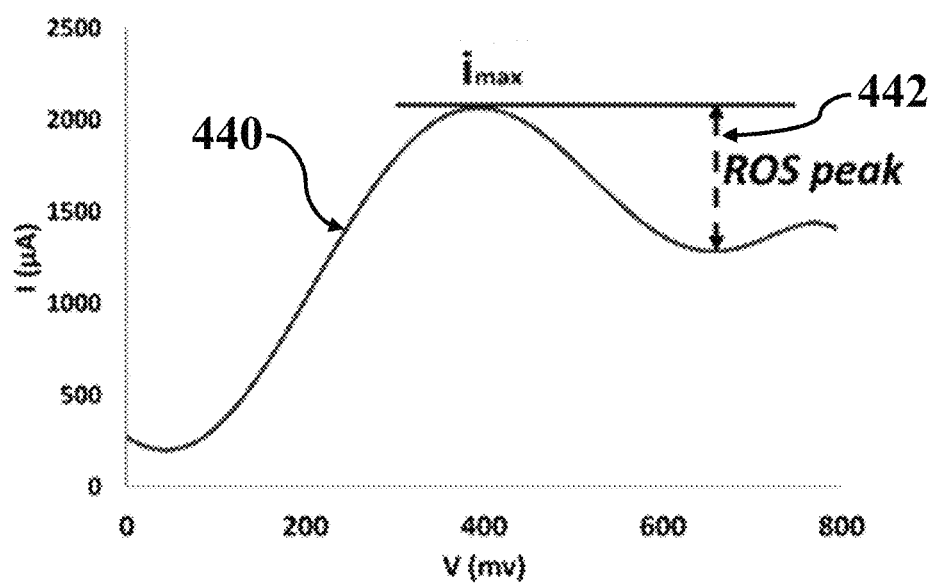
FIG. 4C illustrates an exemplary recorded cyclic voltammetry (CV) pattern from an exemplary sputum sample representing calculation of exemplary current peak, consistent with one or more exemplary embodiments of the present disclosure.

In an exemplary implementation, measuring the level of ROS in sputum sample 432 (step 204) may include recording a cyclic voltammetry (CV) pattern from sputum sample 432 and measuring a current peak of the recorded CV pattern. FIG. 4C shows an exemplary recorded CV pattern 440 from an exemplary sputum sample 432 representing calculation exemplary current peak 442, consistent with one or more exemplary embodiments of the present disclosure.

In an exemplary implementation, recording CV pattern 440 from sputum sample 432 may include attaching a new sensing head 408 to handle 410 of electrochemical probe 402, connecting handle 410 of electrochemical probe 402 to electrochemical stimulator-analyzer 404, inserting three needle-shaped electrodes 412, 414, and 416 into sputum sample 432, applying a sweeping range of electrical potential from about −0.8 V to about +0.8 V with a scan rate of about 100 mVs$^{-1}$ to electrochemical probe 402 utilizing electrochemical stimulator-analyzer 404, and recording CV pattern 440 that may include a set of electrical currents versus the applied swept range of electrical potential.

In an exemplary implementation, inserting three needle-shaped electrodes 412, 414, and 416 into sputum sample 432 may include entering a length of about 2 mm to about 10 mm of three needle-shaped electrodes 412, 414, and 416 into sputum sample 432. Released ROS from sputum sample 432 may interact with array 442 of MWCNTs, array 442 of MWCNTs may be CNT electrodes that may be coated on tips of three needle-shaped electrodes 412, 414, and 416. The CNT electrodes may act as a selective electrochemical tracer of super oxidants, such as $H_2O_2$/ROS. Selective electrochemical reactions of released ROS on MWCNTs may produce a cathodic ionic current peak. Released electric charges due to reaction of ROS molecules on MWCNTs of working electrode 412 may be transferred through counter electrode 414. Hence, quantitative response signals in correlation with viral infection in sputum sample 432 may be obtained and recorded, representing a selective detection of intensity of ROS in sputum sample 432.

In an exemplary embodiment, electrochemical stimulator-analyzer 404 may include a potentiostat device. In an exemplary implementation, electrochemical stimulator-analyzer 404 may be configured to apply electrical potentials to electrochemical probe 402, measure electrical currents that may be generated between working electrode 412 and counter electrode 414 respective to the applied electrical potentials, record the measured electrical currents respective to the applied electrical potentials, and send the recorded and measured electrical currents and applied electrical potentials to processing unit 406.

In an exemplary embodiment, processing unit 406 may include a memory having processor-readable instructions stored therein, and a processor. The processor may be configured to access the memory and execute the processor-readable instructions. The processor may be configured to perform a method similar to one or more steps of exemplary method 200 by executing the processor-readable instructions. The method may include applying a sweeping range of electrical potentials to electrochemical probe 402 utilizing electrochemical stimulator-analyzer 404, measuring a set of generated electrical currents versus the applied sweeping range of electrical potential utilizing electrochemical stimulator-analyzer 404, receiving the set of electrical currents from electrochemical stimulator-analyzer 404, measuring a level of reactive oxygen species (ROS) in sputum sample 432 by measuring a current peak of the set of electrical currents, and detecting a COVID-19 infection status based on the measured level of ROS. In an exemplary implementation, detecting the COVID-19 infection status may include detecting an infection with COVID-19 if the measured current peak is in a first range of current peaks and detecting a non-infection with COVID-19 if the measured current peak is in a second range of current peaks.

In an exemplary embodiment, the first range of current peaks may include a range of current peaks of more than 230 μA. In an exemplary embodiment, the second range of current peaks may include a range of current peaks of less than 190 μA.

In an exemplary implementation, applying the sweeping range of electrical potentials to electrochemical probe 402 may include applying a sweeping range of electrical potentials from −0.8 V to +0.8 V with a scan rate of 100 mVs$^{-1}$ to electrochemical probe 402.

In an exemplary implementation, detecting the COVID-19 infection status may further include detecting a suspicious condition of COVID-19 infection if the measured current peak is in a third range of current peaks between the first range of current peaks and the second range of current peaks. In an exemplary embodiment, the suspicious condition of COVID-19 infection may include an indication that there is no definite determination regarding COVID-19 infection of person 302. In an exemplary embodiment, the third range of current peaks may include a range of current peaks between 190 μA and 230 μA.

In an exemplary implementation, the method may further include generating a calibration data set. In an exemplary implementation, generating the calibration data set may include generating the first range of current peaks by measuring a first set of ROS values of a respective first set of sputum samples acquired from a plurality of persons infected with COVID-19 virus and generating the second range of current peaks by measuring a second set of ROS values of a respective second set of sputum samples acquired from a plurality of persons not infected with COVID-19 virus. In an exemplary implementation, detecting the COVID-19 infection status may further include comparing the measured the measured level of ROS with the ROS values in the calibration data set.

In an exemplary embodiment, processing unit 406 may be configured to record CV pattern 440 based on the applied electrical potentials and the measured electrical currents, which may be sent by electrochemical stimulator-analyzer 404, calculate/measure current peak 442 of CV pattern 440, and detect a COVID-19 infection status of person 302 based on the measured current peak 442 as an indicator of level of ROS in sputum sample 432. In an exemplary embodiment, processing unit 406 may be configured to record CV pattern 440 based on the applied electrical potentials and the measured electrical currents, which may be sent by electrochemical stimulator-analyzer 404, calculate/measure current peak 442 of CV pattern 440, look up the measured current peak 442 in a calibration dataset, and detect a COVID-19 infection status of person 302 based on the measured current peak 442 as an indicator of level of ROS in sputum sample 432. In an exemplary embodiment, processing unit 406 may be further configured to communicate the detected COVID-19 infection status of person 302 to an individual or an expert who may utilize processing unit 406.

Referring again to FIG. 2A, step 206 may include detecting a COVID-19 infection status of person 302 based on the measured level of ROS. In an exemplary implementation, detecting the COVID-19 infection status of person 302 (step 206) may include detecting COVID-19 infection of person 302 if the measured current peak 442 is in a first range of current peaks respective to a range of ROS levels associated with a plurality of persons who may be infected with COVID-19 and detecting COVID-19 non-infection of person 302 if the measured current peak 442 is in a second range of current peaks respective to a range of ROS levels associated with a plurality of persons who may not be infected with COVID-19.

Figure 2B:
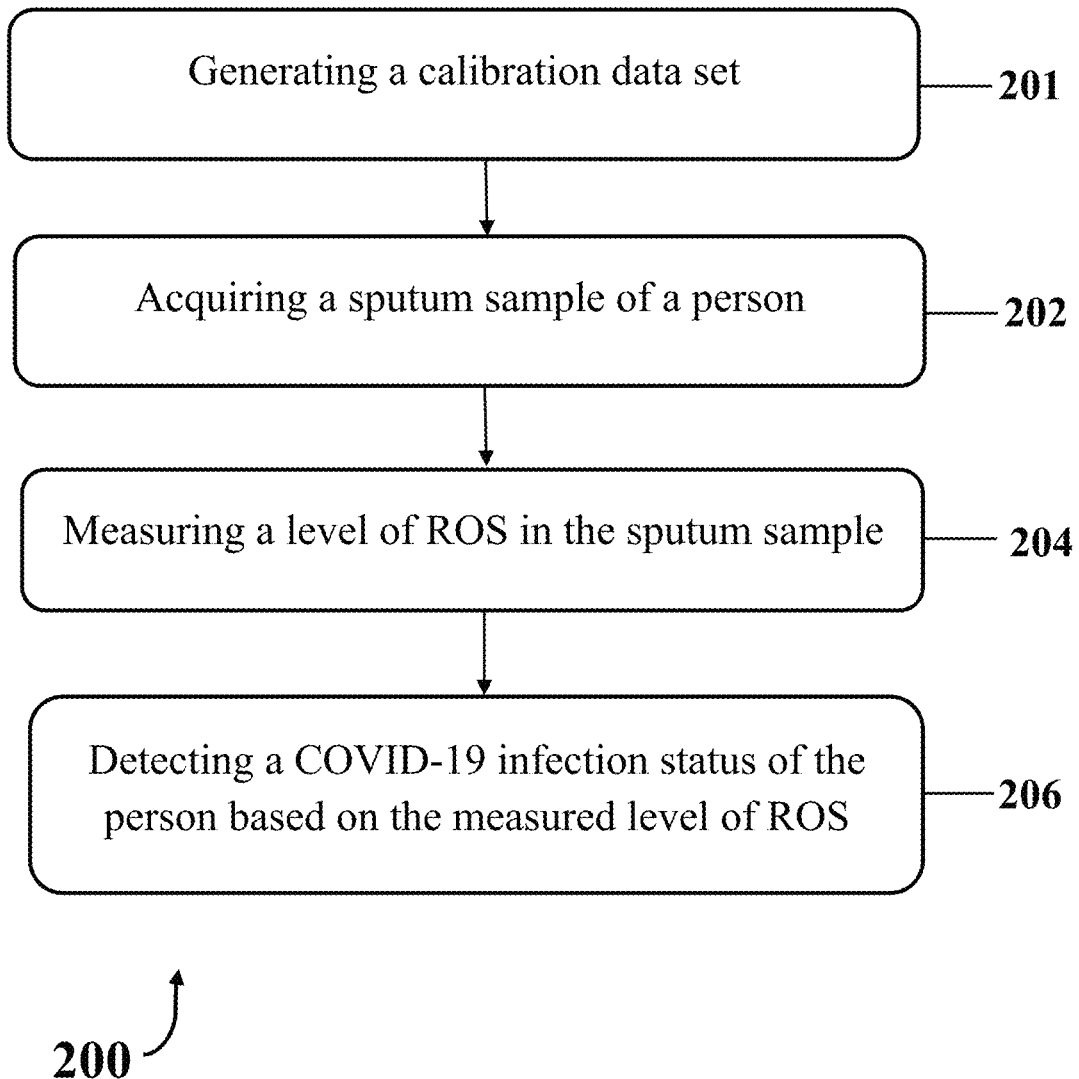
FIG. 2B illustrates another exemplary implementation of the exemplary method for diagnosing COVID-19 infection of a person, consistent with one or more exemplary embodiments of the present disclosure.
Figure 3:
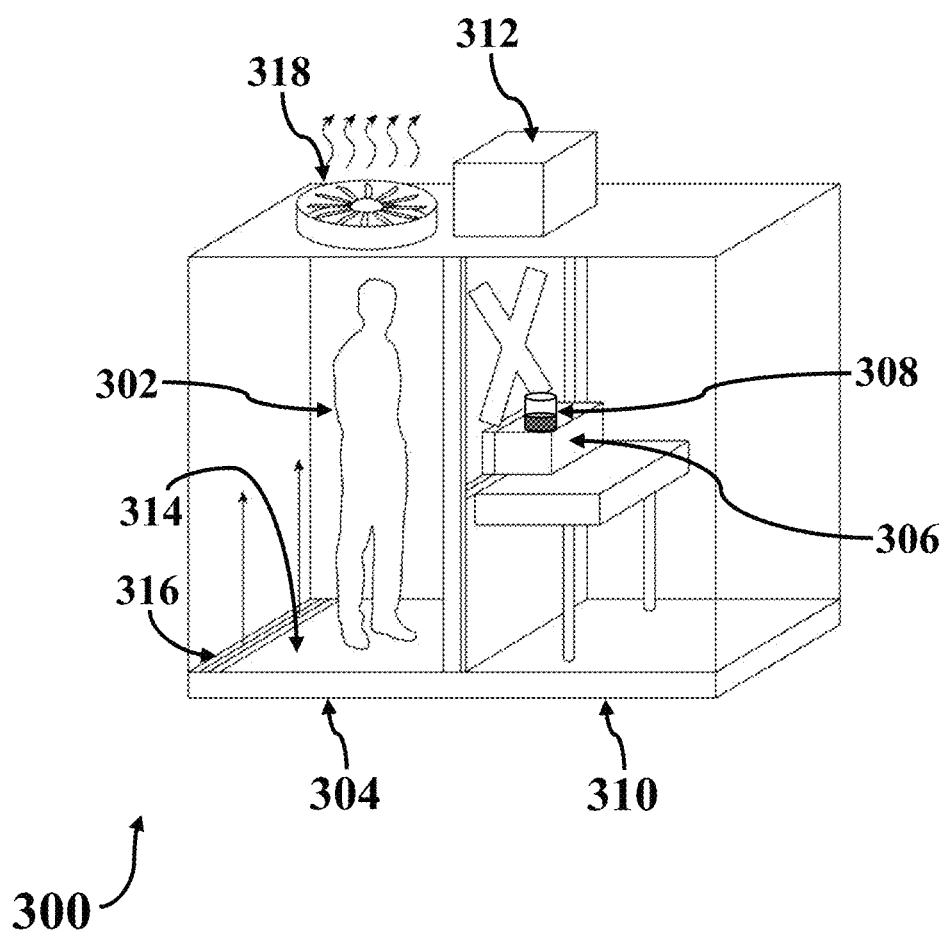
FIG. 3 illustrates a schematic view of an exemplary isolation booth for acquiring an exemplary sputum sample of a person, consistent with one or more exemplary embodiments of the present disclosure.

In an exemplary implementation, exemplary method 200 may further include generating a calibration data set. FIG. 2B shows another exemplary implementation of exemplary method 200 for diagnosing COVID-19 infection of person 302, consistent with one or more exemplary embodiments of the present disclosure. Exemplary method 200 may include generating a calibration data set (step 201), acquiring sputum sample 432 of person 302 (step 202), measuring the level of ROS in sputum sample 432 (step 204), and detecting a COVID-19 infection status of person 302 based on the measured level of ROS (step 206).

In detail, step 201 may include generating a calibration data set. In an exemplary implementation, generating the calibration data set (step 201) may include generating the first range of current peaks associated with a plurality of persons who may be infected with COVID-19 and generating the second range of current peaks associated with a plurality of persons who may not be infected with COVID-19.

In an exemplary implementation, generating the first range of current peaks may include recording a first set of CV patterns from a plurality of persons who may be infected with COVID-19 virus and measuring a first set of current peaks of the respective first set of CV patterns. In an exemplary implementation, generating the second range of current peaks may include recording a second set of CV patterns from a plurality of persons who may not be infected with COVID-19 virus and measuring a second set of current peaks of the respective second set of CV patterns. In an exemplary implementation, generating the first range of current peaks and generating the second range of current peaks may be carried out utilizing system 400 according to a procedure of method 200 of FIG. 2A. In an exemplary implementation, detecting the COVID-19 infection status of person 302 (step 206) may further include looking up the measured current peak 442 in the calibration data set by comparing the measured current peak with current peak values in the calibration data set.

In an exemplary implementation, the calibration data set may include the first range of current peaks of more than about 230 μA for person 302 being infected with COVID-19 virus and the second range of current peaks of less than about 190 μA for person 302 not being infected with in COVID-19 virus. In an exemplary implementation, detecting the COVID-19 infection status of person 302 (step 206) may include detecting COVID-19 infection of person 302 if the measured current peak 442 is in the first range of more than about 230 μA, and detecting COVID-19 non-infection of person 302 if the measured current peak 442 is in the second range of less than about 190 μA.

In an exemplary implementation, detecting the COVID-19 infection status of person 302 (step 206) may further include detecting a suspicious condition of COVID-19 infection of person 302 if the measured current peak 442 is in third range between the first range and the second range. In an exemplary implementation, detecting the COVID-19 infection status of person 302 (step 206) may further include detecting the suspicious condition of COVID-19 infection of person 302 if the measured current peak 442 is in the third range between about 190 μA and about 230 μA. In an exemplary implementation, if the suspicious condition of COVID-19 infection of person 302 is detected, method 200 may further include advising person 302 to remain in a quarantine condition or social isolation over a time period between about 1 day and about 4 days and subsequently, repeating steps 202-206 of method 200.

In an exemplary implementation, method 200 may be utilized for real-time and fast diagnosis of COVID-19 infection of person 302. In an exemplary implementation, measuring the level of ROS in sputum sample (step 204) and detecting the COVID-19 infection status of person 302 (step 206) may be carried out in less than about 30 seconds. In an exemplary implementation, measuring the level of ROS in sputum sample (step 204) and detecting the COVID-19 infection status of person 302 (step 206) may be carried out in less than about 15 seconds. In an exemplary implementation, method 200 may be carried out in a few minutes, for example, in less than 5 minutes for diagnosis of COVID-19 infection of person 302. Accordingly, exemplary embodiments provide an exemplary mechanism for COVID-19 diagnosis which is extremely reliable and efficient.

Figure 5:
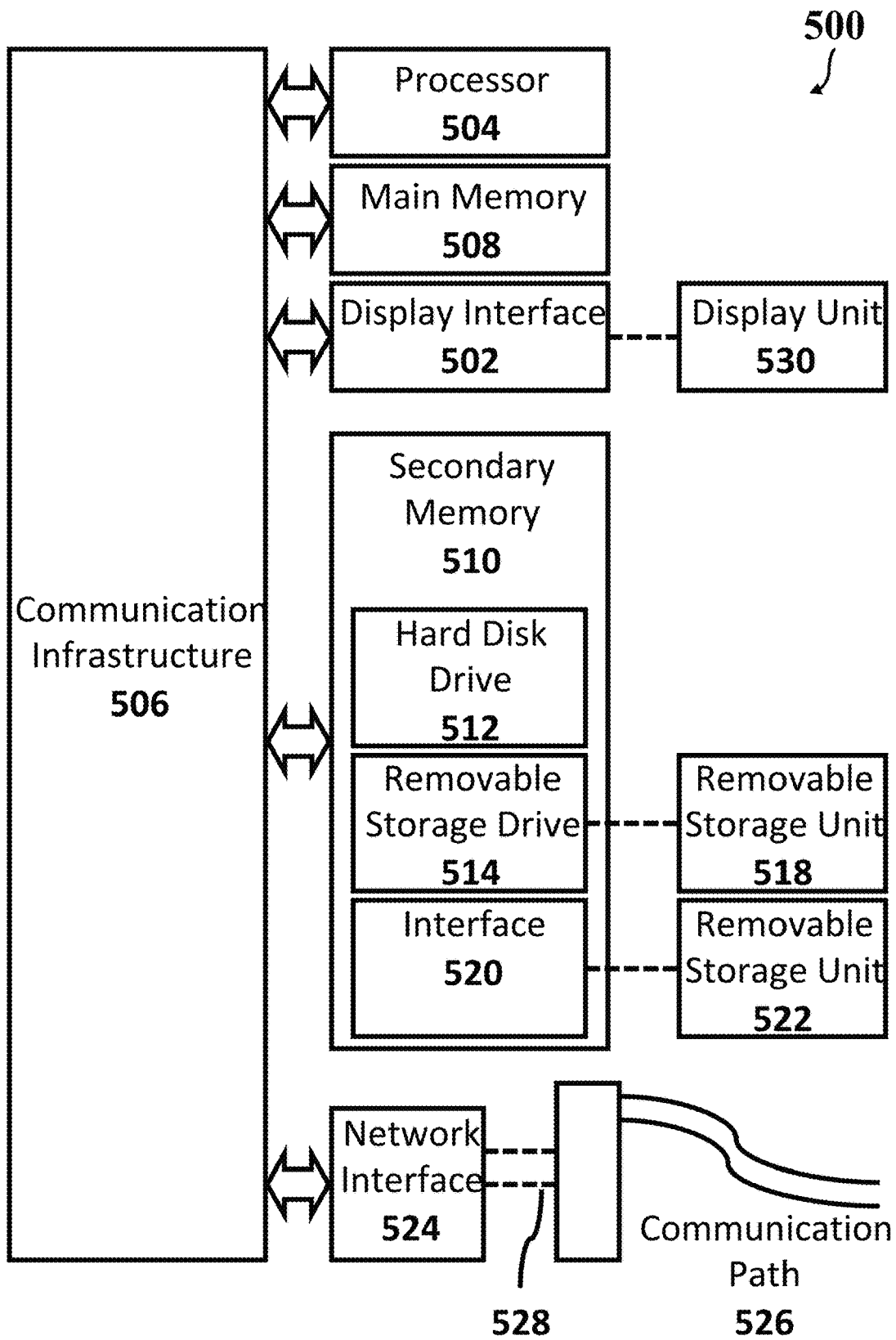
FIG. 5 illustrates an example computer system in which an embodiment of the present disclosure, or portions thereof, may be implemented as computer-readable code, consistent with one or more exemplary embodiments of the present disclosure.

FIG. 5 shows an example computer system 500 in which an embodiment of the present disclosure, or portions thereof, may be implemented as computer-readable code, consistent with one or more exemplary embodiments of the present disclosure. For example, computer system 500 may include an example of processing unit 406, and steps 201, 204, and 206 of flowcharts presented in FIGS. 2A-2B, may be implemented in computer system 500 using hardware, software, firmware, tangible computer readable media having instructions stored thereon, or a combination thereof and may be implemented in one or more computer systems or other processing systems. Hardware, software, or any combination of such may embody any of the modules and components in FIGS. 2A-2B, and FIG. 4.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor cores.

An embodiment of the present disclosure is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 may be connected to a communication infrastructure 506, for example, a bus, message queue, network, or multi-core message-passing scheme.

In an exemplary embodiment, computer system 500 may include a display interface 502, for example a video connector, to transfer data to a display unit 530, for example, a monitor. Computer system 500 may also include a main memory 508, for example, random access memory (RAM), and may also include a secondary memory 510. Secondary memory 510 may include, for example, a hard disk drive 512, and a removable storage drive 514. Removable storage drive 514 may include a floppy disk drive, a magnetic tape drive, an optical disk drive, a flash memory, or the like. Removable storage drive 514 may read from and/or write to a removable storage unit 518 in a well-known manner. Removable storage unit 518 may include a floppy disk, a magnetic tape, an optical disk, etc., which may be read by and written to by removable storage drive 514. As will be appreciated by persons skilled in the relevant art, removable storage unit 518 may include a computer usable storage medium having stored therein computer software and/or data.

In alternative implementations, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524.

These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement different embodiments of the present disclosure as discussed herein. In particular, the computer programs, when executed, enable processor device 504 to implement the processes of the present disclosure, such as the operations in method 200 illustrated by FIGS. 2A-2B, discussed above. Accordingly, such computer programs represent controllers of computer system 500. Where an exemplary embodiment of method 100 is implemented using software, the software may be stored in a computer program product and loaded into computer system 500 using removable storage drive 514, interface 520, and hard disk drive 512, or communications interface 524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

EXAMPLE 1: REAL-TIME DIAGNOSIS OF REACTIVE OXYGEN SPECIES (ROS) IN FRESH SPUTUM BY ELECTROCHEMICAL TRACING

In this example, an exemplary system similar to system 400 was utilized to process an exemplary method similar to method 200 for testing more than 140 normal (not-infected with COVID-19) and infected cases with COVID-19, obtaining a calibration dataset, and screening infected persons from others. The current peak results were compared by clinical diagnostics standards (CT-Scan, CBC test, and RT-PCR) in infected or non-infected COVID-19 individuals, so a calibration pattern was achieved. The calibrated probe 402 then was utilized on more than 30 patients and showed accuracy of 94% and sensitivity of 92% with respect to CT-Scan as the gold standard.

All patients with suspected COVID-19 provided written informed consent according to an ethically approved protocol for the use of their samples. Descriptive data on patients with laboratory-confirmed COVID-19 infection were collected and analyzed by real-time RT-PCR assays and clinical judgment (HR-CT, ESR, CRP, CBC, Lymphopenia, and observational symptoms). Clinical, laboratory, and radiological characteristics and diagnosis and outcomes data were collected from all patients. Fresh sputum samples prepared from 172 patients who had been admitted to the intensive care unit (ICU) and those who had not were recorded. An expert team also communicated with patients or their families to record their epidemiological and symptom data. Outcomes were also compared between patients who were hospitalized in ICU (ranged from 1 to 10 days of ICU care), patients who were hospitalized and didn't need the ICU care, non-hospitalized candidates who were tested by RT-PCR, and/or CT for COVID-19 diagnosis and normal candidates with confirmed non-infection with COVID-19.

An exemplary probe similar to exemplary probe 402 was fabricated by growth of MWCNTs on tip of steel needles in the conformation of three electrodes, including working electrode (WE), counter electrode (CE), and reference electrode (RE), with a triangular distance of about 3 mm from each other. Also, an exemplary processing unit similar to processing unit 406 was designed based on generated calibration data set to analyze the data and diagnose whether the responses are related to the positive or negative detection of COVID-19. This ability of the exemplary system 400 may provide a free and flexible method for the phlebotomist or physicians to utilize system 400 in the laboratories or clinics. A sputum sample was taken from (or acquired of) each person, and exemplary probe 402 was entered to sputum sample. For electrochemical measurements, electrical potential was swept in a range from about −0.8 to about +0.8 V, using a scan rate of 100 mVs$^{-1}$ as known parameters in biological solutions. The COVID-19 infection in suspicious cases was detected in less than about 30 seconds. Utilizing this procedure, a calibration related to COVID-19 was performed by testing about 170 normal, suspicious, and virus-infected cases. It showed great promising results in the real-time screening of people during this pandemic.

The detailed information of 172 candidates who were known cases of positive and negative COVID-19 confirmed by clinical judgment (HR-CT-Scan, ESR, CRP, CBC, Lymphopenia, and observational symptoms) and RT-PCR assays, are presented in Table 1. HR-CT was done only for suspicious patients, but other tests were done for both suspicious and non-suspicious cases.

TABLE 1

| Baseline characteristics and symptoms of 172 patients who were investigated in this example | | | | | |
|---|---|---|---|---|---|
| Characteristics and symptoms | All Patients (n = 172) | ICU care (n = 25) | Hospitalized without need to ICU care (n = 36) | Non-hospitalized candidates checked by RT-PCR or CT-Scan (n = 75) | Normal candidates with non-infection with COVID-19 (n = 36) |
| Characteristics | | | | | |
| Age | 46.3 (21-76) | 53.7 (41-65) | 47 (21-76) | 45.3 (24-58) | 39.1 (22-60) |
| Sex | | | | | |
| Female | 67 (39%) | 8 (32%) | 12 (33%) | 32 (43%) | 15 (42%) |
| Male | 105 (61%) | 17 (68%) | 24 (67%) | 43 (57%) | 21 (58%) |
| Race | White | White | White | White | White |
| Current Smoking | 28 (16%) | 0 | 2 (6%) | 19 (25%) | 7 (19%) |
| Any comorbidity | | | | | |
| Diabetes | 30 (17%) | 9 (36%) | 7 (19%) | 12 (16%) | 2 (6%) |
| Hypertension | 14 (8%) | 6 (24%) | 3 (8%) | 5 (7%) | 0 |

TABLE 1-continued

Baseline characteristics and symptoms of 172 patients who were investigated in this example

| Characteristics and symptoms | All Patients (n = 172) | ICU care (n = 25) | Hospitalized without need to ICU care (n = 36) | Non-hospitalized candidates checked by RT-PCR or CT-Scan (n = 75) | Normal candidates with non-infection with COVID-19 (n = 36) |
|---|---|---|---|---|---|
| pulmonary disease | 2 (1%) | 2 (8%) | 0 | 0 | 0 |
| Cardiovascular disease | 11 (6%) | 5 (20%) | 3 (8%) | 2 (3%) | 1 (3%) |
| Chronic liver disease | 6 (3%) | 1 (4%) | 2 (6%) | 3 (4%) | 0 |
| Hypothyroidism | 21 (12%) | 3 (12%) | 2 (6%) | 13 (17%) | 3 (8%) |
| Hyperthyroidism | 7 (4%) | 1 (4%) | 0 | 6 (8%) | 0 |
| Immune deficiency disease | 1 (1%) | 1 (4%) | 0 | 0 | 0 |
| symptoms | | | | | |
| Fever | 107 (62%) | 25 (100%) | 34 (94%) | 42 (56%) | 6 (17%) |
| Cough | 84 (49%) | 23 (92%) | 31 (86%) | 25 (34%) | 5 (14%) |
| Myalgia or fatigue | 75 (44%) | 22 (88%) | 29 (81%) | 22 (29%) | 2 (6%) |
| Dyspnoea | 72 (42%) | 24 (96%) | 28 (78%) | 18 (24%) | 2 (6%) |
| Diarrhoea | 4 (2%) | 0 | 2 (6%) | 2 (3%) | 0 |
| Vomit | 11 (6%) | 2 (8%) | 2 (6%) | 7 (9%) | 0 |
| Headache | 47 (27%) | 5 (20%) | 12 (33%) | 27 (36%) | 3 (8%) |
| Lack of appetite | 80 (47%) | 22 (88%) | 31 (86%) | 25 (33%) | 2 (6%) |
| Vertigo | 6 (3%) | 2 (8%) | 4 (11%) | 0 | 0 |
| Chest pain | 14 (8%) | 4 (16%) | 7 (19%) | 3 (4%) | 0 |
| Sore throat | 36 (21%) | 1 (4%) | 5 (14%) | 25 (33%) | 5 (14%) |
| Haemoptysis | 2 (1%) | 1 (4%) | 1 (3%) | 0 | 0 |

Meaningful results were achieved in a way that a calibration pattern was provided between the responses utilizing exemplary system 400 and the clinical state of the patients. About 92% of patients with severe symptoms who were hospitalized in ICU (ranged from 1 to 10 days of ICU care) showed peak currents in a range of about 230-1500 µA, about 100% of the patients with moderate symptoms who were hospitalized with no need for ICU showed current peaks in a range of about 315-1560 µA. About 83% of negative COVID-19 cases due to RT-PCR results showed peak currents lower than about 180 µA. About 94% of normal candidates with no complaint cases (including some nurses and healthy people) who were clinically checked by physicians in hospitals and confirmed as non-COVID-19 cases showed peak currents lower than about 190 µA. Among all of the cases whose COVID-19 were confirmed by CBC and CT-Scan results (as a clinical gold standard), about 95% showed peak currents higher than about 230 µA. Hence, peak currents higher than about 230 µA were considered as the positive score of the present disclosed system and method.

Moreover, among non-hospitalized COVID-19 free cases who were clinically checked by physicians and diagnosed as normal cases, about 94% showed current peaks lower than about 200 µA. Among the patients whose COVID-19-free diagnosis was just carried out by RT-PCR, about 84% showed current peaks lower than about 200 µA. In this regard, a calibrated diagnostic cut-off based on CBC/CT-Scan gold standard results were defined for the scores detected by exemplary system 400, including: current peaks lower than about 190 µA were scored as COVID-19-Free cases, in a range of about 190-230 µA were scored as suspicious cases who were recommended to do CT-Scan, and current peaks higher than about 230 µA were scored as COVID-19-Positive cases.

Figure 6:
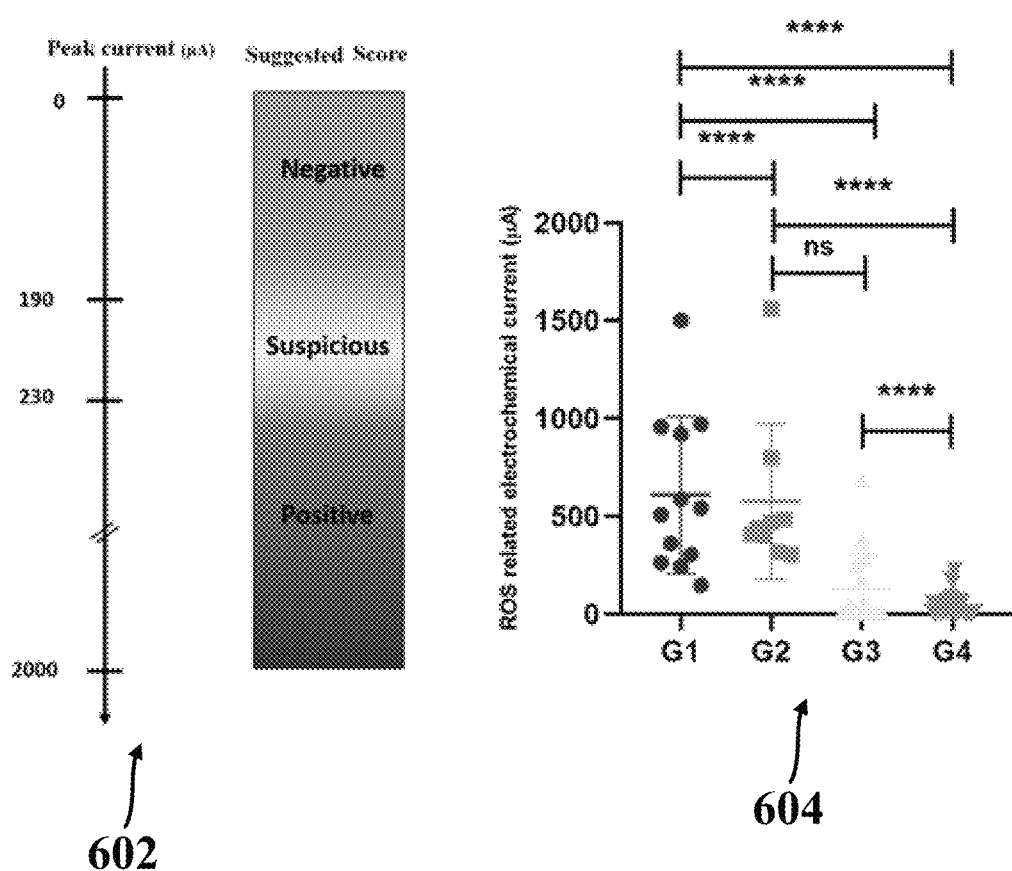
FIG. 6 illustrates a calibration pattern obtained from 142 candidates who were known cases of positive and negative COVID-19 confirmed by clinical judgment (HR-CT, ESR, CRP, CBC, Lymphopenia, and observational symptoms), and RT-PCR assays, and comparative diagnostic results of each group expressed as mean±SD, consistent with one or more exemplary embodiments of the present disclosure.

FIG. 6 shows a calibration pattern 602 obtained from 142 candidates who were known cases of positive and negative COVID-19 confirmed by clinical judgment (HR-CT, ESR, CRP, CBC, Lymphopenia, and observational symptoms), and RT-PCR assays, and comparative diagnostic results 604 of each group expressed as mean±SD, consistent with one or more exemplary embodiments of the present disclosure. Based on calibration pattern 602, the validated diagnostic ranges of the exemplary method and system for positive, suspicious, and negative ranges were obtained as higher than about 230 µA, about 190-230 µA, and lower than about 190 µA, respectively. Comparative diagnostic results 604 of each group were expressed as mean±SD and analyzed using a one-way ANOVA method followed by Tukey's multiple comparisons test. The p-value amount of each group are shown in this figure. Differences in mean current peak responses between infected and non-infected patients with COVID-19 were highly significant (G1 versus G4: p<0.0001, G2 versus G4: p<0.0001), and NS: non-significant. G1, G2, G3, and G4 refers to the patients who were hospitalized in ICU (n=25), hospitalized without need to ICU care (n=36), Non-hospitalized candidates which were checked by RT-PCR (n=45), and normal candidates with confirmed non-infection with COVID-19 (n=36), respectively.

Figure 7A:
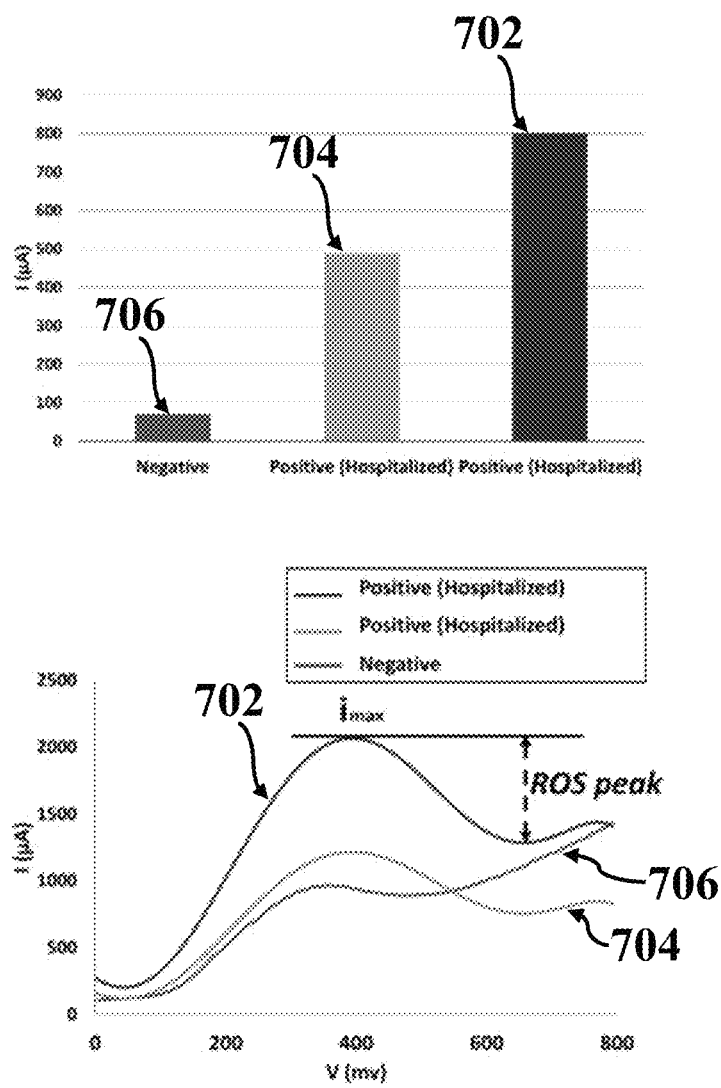
FIG. 7A illustrates ROS related electrochemical cyclic voltammetry cathodic peaks from fresh sputum of two different patients ID 34 and ID 37 who were infected with COVID-19 and hospitalized in comparison with a confirmed normal case, consistent with one or more exemplary embodiments of the present disclosure.
Figure 7B:
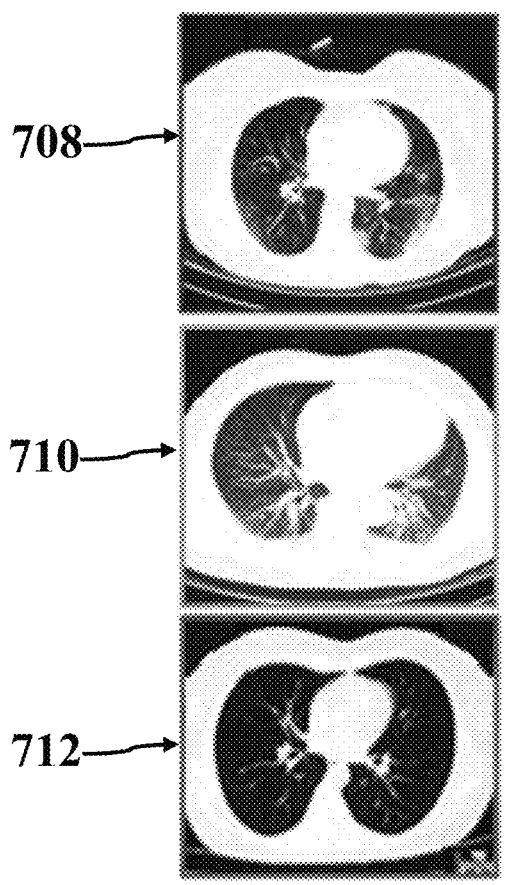
FIG. 7B illustrates lung's CT-Scan of the patients ID 34 and ID 37 infected with COVID-19 and hospitalized in comparison with the confirmed normal case, consistent with one or more exemplary embodiments of the present disclosure.

FIG. 7A shows ROS related electrochemical cyclic voltammetry cathodic peaks from fresh sputum of two different patients ID 34 (designated by 702) and ID 37 (designated by 704) were infected with COVID-19 and hospitalized in comparison with a confirmed normal case (designated by 706), consistent with one or more exemplary embodiments of the present disclosure. FIG. 7B shows lung's CT-Scan of the patients ID 34 (image 708) and ID 37 (image 710) infected with COVID-19 and hospitalized in comparison with the confirmed normal case (image 712), consistent with one or more exemplary embodiments of the present disclosure. It may be observed from these figures that the intensity of the electrochemical ROS peak currents may be correlated with the amount of the viral-induced mitochondrial ROS production found in the sputum. It is meaningfully higher in the sputum sample of the patient ID 34 (I=800 µA) than patient ID 37 (I=490 µA) with severe lung affected by COVID-19 viruses. The CT-Scan of the patient ID 34's lung showed more distinctive hazy patches with gross glassy opacity in both lobes of the lung. Also, a normal candidate with no complaint's cases who were clinically checked by a physician in hospital and confirmed as non-COVID-19 cases showed peak current 71 µA. The CT-Scan of this patient showed blood vessels without any viral infection effects.

In addition to 142 cases were tested for generating calibration pattern, the donated sputum from 30 patients (collected from 4 individual medical centers) who were recommended to do CT-Scan by the physicians (due to their blood tests and physical symptoms), were tested and scored by the exemplary method and system (presented in Table 1). 13/30 of the patients were diagnoses as positive COVID-19 cases, in which 12/13 of those cases were confirmed by CT-Scan images. Just one case was scored as suspicious, which was not confirmed as positive COVID-19 by CT-Scan. 17/30 of the cases were negatively scored by the disclosed procedure, among which just one case showed COVID-19 positive CT-Scan result. So, discrepancies between the results of the exemplary procedure and clinical judgment on those 30 patients were less than about 7% with false negatives of less than about 3%. Table 2 shows comparative diagnostic results of the exemplary system/method for group (A) including 142 candidates who were known cases of positive and negative COVID-19 confirmed by clinical judgment (HR-CT, ESR, CRP, CBC, Lymphopenia and observational symptoms) and RT-PCR assays, and group (B) including donated sputum from 30 patients who were recommended to do CT-Scan by the physicians (due to their blood tests and physical symptoms).

TABLE 2

Comparative diagnostic results of group (A) 142 candidates who were known cases of positive and negative COVID-19 confirmed by clinical judgment and RT-PCR assays, and group (B) donated sputum from 30 patients who were recommended to do CT-Scan by the physicians due to their blood tests and physical symptoms.

| Diagnosis results | A (n = 142) | B (n = 30) |
|---|---|---|
| TP | 61 | 12 |
| TN | 72 | 16 |
| FP | 7 | 1 |
| FN | 2 | 1 |
| Accuracy | 97% | 94% |
| Sensitivity | 97% | 92% |
| Specificity | 91% | 94% |
| Selectivity | 88% | 87% |

Also, two COVID-free patients with oral disease and Purulent sore throat that may induce ROS in sputum samples were checked by the exemplary procedure, which showed current peaks as low as about 70 µA (Patients ID 6 and 22 in Table 4). Hence, non-COVID-19 based ROS accumulated in sputum samples might not perturb the results for COVID-19 detection.

Table 3 shows comparative diagnostic results of 142 candidates who were known cases of positive and negative COVID-19 confirmed by clinical judgment assays and RT-PCR assays, and the present COVID-19 ROS diagnosis system. G1, G2, G3, and G4 refers to the patients who were hospitalized in ICU (n=25), hospitalized without need to ICU care (n=36), non-hospitalized candidates which were checked by RT-PCR (n=45), and normal candidates with confirmed non-infection with COVID-19 (n=36), respectively.

TABLE 3

Comparative diagnostic results of 142 candidates who were known cases of positive and negative COVID-19 confirmed by clinical judgment and RT-PCR assays, and the present COVID-19 ROS diagnosis system.

| ID | Patient status | Gender | Age | Time of infection | Time of test | current peak (I) (µA) | Other technics diagnosis | Present diagnosis vs. other technics |
|---|---|---|---|---|---|---|---|---|
| 1 | G1 | M | 57 | Apr. 10, 2020 | $2^{th}$ days of admission | 1500 | + | TP |
| 2 | G1 | M | 41 | Apr. 15, 2020 | $3^{th}$ days of admission | 360 | + | TP |
| 3 | G1 | F | 45 | Apr. 14, 2020 | $5^{th}$ days of admission | 263 | + | TP |
| 4 | G1 | M | 57 | Apr. 9, 2020 | $2^{th}$ days of admission | 957 | + | TP |
| 5 | G1 | M | 50 | Apr. 16, 2020 | $2^{th}$ days of admission | 920 | + | TP |
| 6 | G1 | F | 57 | Apr. 13, 2020 | $6^{th}$ days of admission | 147 | + | FN |
| 7 | G1 | M | 50 | Apr. 9, 2020 | $7^{th}$ days of admission | 234 | + | TP |
| 8 | G1 | F | 33 | Apr. 10, 2020 | $4^{th}$ days of admission | 508 | + | TP |
| 9 | G1 | F | 65 | Apr. 10, 2020 | $4^{th}$ days of admission | 304 | + | TP |
| 10 | G1 | M | 65 | Apr. 15, 2020 | $1^{th}$ day of admission | 543 | + | TP |
| 11 | G1 | M | 61 | Apr. 14, 2020 | $5^{th}$ days of admission | 971 | + | TP |
| 12 | G1 | M | 58 | Apr. 8, 2020 | $5^{th}$ days of admission | 588 | + | TP |
| 13 | G1 | M | 59 | Apr. 11, 2020 | $3^{th}$ days of admission | 1420 | + | TP |
| 14 | G1 | M | 60 | Apr. 11, 2020 | $8^{th}$ days of admission | 260.3 | + | TP |
| 15 | G1 | M | 48 | Apr. 10, 2020 | $2^{th}$ days of admission | 353 | + | TP |
| 16 | G1 | M | 53 | Apr. 9, 2020 | $1^{th}$ day of admission | 734.7 | + | TP |
| 17 | G1 | M | 55 | Apr. 14, 2020 | $4^{th}$ days of admission | 520 | + | TP |
| 18 | G1 | M | 61 | Apr. 10, 2020 | $2^{th}$ days of admission | 247 | + | TP |
| 19 | G1 | F | 50 | Apr. 9, 2020 | $8^{th}$ days of admission | 183.5 | + | FN |
| 20 | G1 | M | 48 | Apr. 11, 2020 | $5^{th}$ days of admission | 318.2 | + | TP |
| 21 | G1 | F | 49 | Apr. 13, 2020 | $3^{th}$ days of admission | 297.6 | + | TP |
| 22 | G1 | F | 57 | Apr. 10, 2020 | $9^{th}$ days of admission | 316 | + | TP |
| 23 | G1 | M | 58 | Apr. 12, 2020 | $4^{th}$ days of admission | 871 | + | TP |

TABLE 3-continued

Comparative diagnostic results of 142 candidates who were known cases of positive and negative COVID-19 confirmed by clinical judgment and RT-PCR assays, and the present COVID-19 ROS diagnosis system.

| ID | Patient status | Gender | Age | Time of infection | Time of test | current peak (I) (μA) | Other technics diagnosis | Present diagnosis vs. other technics |
|---|---|---|---|---|---|---|---|---|
| 24 | G1 | M | 55 | Apr. 10, 2020 | 5$^{th}$ days of admission | 368.6 | + | TP |
| 25 | G1 | F | 51 | Apr. 12, 2020 | 7$^{th}$ days of admission | 255.8 | + | TP |
| 26 | G2 | F | 47 | Apr. 10, 2020 | 3$^{th}$ days of admission | 317 | + | TP |
| 27 | G2 | M | 35 | Apr. 12, 2020 | 1$^{th}$ days of admission | 340 | + | TP |
| 28 | G2 | M | 52 | Apr. 12, 2020 | 4$^{th}$ days of admission | 469.1 | + | TP |
| 29 | G2 | M | 30 | Apr. 13, 2020 | 4$^{th}$ days of admission | 439.9 | + | TP |
| 30 | G2 | F | 21 | Apr. 11, 2020 | 1$^{th}$ days of admission | 438.9 | + | TP |
| 31 | G2 | M | 76 | Apr. 11, 2020 | 3$^{th}$ days of admission | 1561.5 | + | TP |
| 32 | G2 | M | 30 | Apr. 10, 2020 | 2$^{th}$ days of admission | 409 | + | TP |
| 33 | G2 | F | 44 | Apr. 12, 2020 | 2$^{th}$ days of admission | 400 | + | TP |
| 34 | G2 | F | 28 | Apr. 13, 2020 | 3$^{th}$ days of admission | 800 | + | TP |
| 35 | G2 | M | 50 | Apr. 14, 2020 | 5$^{th}$ days of admission | 427.3 | + | TP |
| 36 | G2 | M | 52 | Apr. 8, 2020 | 1$^{th}$ days of admission | 328 | + | TP |
| 37 | G2 | M | 66 | Apr. 10, 2020 | 6$^{th}$ days of admission | 490 | + | TP |
| 38 | G2 | F | 67 | Apr. 12, 2020 | 7$^{th}$ days of admission | 501 | + | TP |
| 39 | G2 | M | 48 | Apr. 12, 2020 | 4$^{th}$ days of admission | 349.7 | + | TP |
| 40 | G2 | M | 49 | Apr. 11, 2020 | 4$^{th}$ days of admission | 335.2 | + | TP |
| 41 | G2 | M | 51 | Apr. 10, 2020 | 6$^{th}$ days of admission | 478.6 | + | TP |
| 42 | G2 | M | 53 | Apr. 7, 2020 | 5$^{th}$ days of admission | 401.4 | + | TP |
| 43 | G2 | F | 60 | Apr. 12, 2020 | 5$^{th}$ days of admission | 357 | + | TP |
| 44 | G2 | M | 52 | Apr. 13, 2020 | 4$^{th}$ days of admission | 315.6 | + | TP |
| 45 | G2 | M | 48 | Apr. 10, 2020 | 3$^{th}$ days of admission | 529 | + | TP |
| 46 | G2 | M | 46 | Apr. 9, 2020 | 2$^{th}$ days of admission | 756 | + | TP |
| 47 | G2 | M | 63 | Apr. 12, 2020 | 1$^{th}$ days of admission | 316 | + | TP |
| 48 | G2 | M | 32 | Apr. 13, 2020 | 1$^{th}$ days of admission | 322.7 | + | TP |
| 49 | G2 | F | 54 | Apr. 9, 2020 | 5$^{th}$ days of admission | 478 | + | TP |
| 50 | G2 | F | 55 | Apr. 10, 2020 | 10$^{th}$ days of admission | 500 | + | TP |
| 51 | G2 | M | 41 | Apr. 10, 2020 | 7$^{th}$ days of admission | 504.6 | + | TP |
| 52 | G2 | M | 66 | Apr. 13, 2020 | 6$^{th}$ days of admission | 357.9 | + | TP |
| 53 | G2 | F | 72 | Apr. 12, 2020 | 2$^{th}$ days of admission | 456.4 | + | TP |
| 54 | G2 | F | 48 | Apr. 10, 2020 | 3$^{th}$ days of admission | 308.4 | + | TP |
| 55 | G2 | F | 30 | Apr. 10, 2020 | 3$^{th}$ days of admission | 391 | + | TP |
| 56 | G2 | M | 28 | Apr. 9, 2020 | 1$^{th}$ days of admission | 378.7 | + | TP |
| 57 | G2 | M | 35 | Apr. 14, 2020 | 4$^{th}$ days of admission | 438.3 | + | TP |
| 58 | G2 | F | 42 | Apr. 10, 2020 | 5$^{th}$ days of admission | 499.5 | + | TP |
| 59 | G2 | M | 42 | Apr. 8, 2020 | 2$^{th}$ days of admission | 410.3 | + | TP |
| 60 | G2 | M | 48 | Apr. 10, 2020 | 2$^{th}$ days of admission | 375.9 | + | TP |
| 61 | G2 | M | 31 | Apr. 7, 2020 | 6$^{th}$ days of admission | 397.6 | + | TP |
| 62 | G3 | M | 50 | Apr. 14, 2020 | 2$^{th}$ days after appearance of symptoms | 275 | − | FP |
| 63 | G3 | F | 55 | Apr. 10, 2020 | 6$^{th}$ days after appearance of symptoms | 18 | − | TN |
| 64 | G3 | M | 54 | Apr. 10, 2020 | 7$^{th}$ days after appearance of symptoms | 689 | + | TP |
| 65 | G3 | M | 50 | Apr. 15, 2020 | 8$^{th}$ days after appearance of symptoms | 164 | − | TN |
| 66 | G3 | F | 45 | Apr. 19, 2020 | 4$^{th}$ days after appearance of symptoms | 41.9 | − | TN |
| 67 | G3 | F | 37 | Apr. 20, 2020 | 3$^{th}$ days after appearance of symptoms | 17 | − | TN |
| 68 | G3 | F | 39 | Apr. 19, 2020 | 4$^{th}$ days after appearance of symptoms | 10.9 | − | TN |
| 69 | G3 | F | 45 | Apr. 14, 2020 | 6$^{th}$ days after appearance of symptoms | 0 | − | TN |
| 70 | G3 | M | 52 | Apr. 15, 2020 | 8$^{th}$ days after appearance of symptoms | 7.7 | − | TN |
| 71 | G3 | F | 41 | Apr. 16, 2020 | 5$^{th}$ days after appearance of symptoms | 382 | + | TP |
| 72 | G3 | M | 51 | Apr. 13, 2020 | 4$^{th}$ days after appearance of symptoms | 320 | − | FP |
| 73 | G3 | M | 44 | Apr. 19, 2020 | 4$^{th}$ days after appearance of symptoms | 0 | − | TN |
| 74 | G3 | F | 48 | Apr. 18, 2020 | 5$^{th}$ days after appearance of symptoms | 3.5 | − | TN |
| 75 | G3 | F | 43 | Apr. 14, 2020 | 7$^{th}$ days after appearance of symptoms | 11.7 | − | TN |
| 76 | G3 | M | 47 | Apr. 15, 2020 | 5$^{th}$ days after appearance of symptoms | 63.9 | − | TN |
| 77 | G3 | F | 45 | Apr. 15, 2020 | 7$^{th}$ days after appearance of symptoms | 255 | − | FP |
| 78 | G3 | M | 50 | Apr. 13, 2020 | 7$^{th}$ days after appearance of symptoms | 5.3 | − | TN |
| 79 | G3 | F | 48 | Apr. 18, 2020 | 5$^{th}$ days after appearance of symptoms | 156.9 | − | TN |
| 80 | G3 | M | 41 | Apr. 17, 2020 | 3$^{th}$ days after appearance of symptoms | 10.7 | − | TN |
| 81 | G3 | M | 42 | Apr. 17, 2020 | 3$^{th}$ days after appearance of symptoms | 4.3 | − | TN |
| 82 | G3 | F | 50 | Apr. 20, 2020 | 4$^{th}$ days after appearance of symptoms | 5.9 | − | TN |
| 83 | G3 | F | 50 | Apr. 17, 2020 | 5$^{th}$ days after appearance of symptoms | 0 | − | TN |
| 84 | G3 | F | 50 | Apr. 12, 2020 | 5$^{th}$ days after appearance of symptoms | 12 | − | TN |
| 85 | G3 | M | 28 | Apr. 14, 2020 | 5$^{th}$ days after appearance of symptoms | 57.6 | − | TN |
| 86 | G3 | M | 43 | Apr. 14, 2020 | 5$^{th}$ days after appearance of symptoms | 31.2 | − | TN |
| 87 | G3 | F | 39 | Apr. 15, 2020 | 6$^{th}$ days after appearance of symptoms | 0.7 | − | TN |
| 88 | G3 | F | 49 | Apr. 18, 2020 | 4$^{th}$ days after appearance of symptoms | 1 | − | TN |
| 89 | G3 | F | 48 | Apr. 17, 2020 | 6$^{th}$ days after appearance of symptoms | 45 | − | TN |
| 90 | G3 | F | 53 | Apr. 13, 2020 | 5$^{th}$ days after appearance of symptoms | 72 | − | TN |
| 91 | G3 | F | 24 | Apr. 14, 2020 | 4$^{th}$ days after appearance of symptoms | 36 | − | TN |
| 92 | G3 | F | 38 | Apr. 14, 2020 | 4$^{th}$ days after appearance of symptoms | 2 | − | TN |
| 93 | G3 | M | 34 | Apr. 13, 2020 | 7$^{th}$ days after appearance of symptoms | 7 | − | TN |
| 94 | G3 | M | 42 | Apr. 14, 2020 | 7$^{th}$ days after appearance of symptoms | 34 | − | TN |
| 95 | G3 | M | 33 | Apr. 16, 2020 | 4$^{th}$ days after appearance of symptoms | 77 | − | TN |
| 96 | G3 | F | 39 | Apr. 16, 2020 | 5$^{th}$ days after appearance of symptoms | 81 | − | TN |

TABLE 3-continued

Comparative diagnostic results of 142 candidates who were known cases of positive and negative COVID-19 confirmed by clinical judgment and RT-PCR assays, and the present COVID-19 ROS diagnosis system.

| ID | Patient status | Gender | Age | Time of infection | Time of test | current peak (I) (µA) | Other technics diagnosis | Present diagnosis vs. other technics |
|---|---|---|---|---|---|---|---|---|
| 97 | G3 | M | 31 | Apr. 20, 2020 | 3$^{th}$ days after appearance of symptoms | 36 | – | TN |
| 98 | G3 | M | 40 | Apr. 21, 2020 | 2$^{th}$ days after appearance of symptoms | 5.6 | – | TN |
| 99 | G3 | M | 51 | Apr. 14, 2020 | 7$^{th}$ days after appearance of symptoms | 7 | – | TN |
| 100 | G3 | M | 52 | Apr. 16, 2020 | 7$^{th}$ days after appearance of symptoms | 9 | – | TN |
| 101 | G3 | M | 49 | Apr. 15, 2020 | 5$^{th}$ days after appearance of symptoms | 278.3 | – | FP |
| 102 | G3 | M | 48 | Apr. 18, 2020 | 5$^{th}$ days after appearance of symptoms | 28 | – | TN |
| 103 | G3 | M | 51 | Apr. 16, 2020 | 4$^{th}$ days after appearance of symptoms | 36 | – | TN |
| 104 | G3 | M | 50 | Apr. 16, 2020 | 4$^{th}$ days after appearance of symptoms | 8 | – | TN |
| 105 | G3 | M | 47 | Apr. 16, 2020 | 7$^{th}$ days after appearance of symptoms | 299 | – | FP |
| 106 | G3 | M | 58 | Apr. 18, 2020 | 5$^{th}$ days after appearance of symptoms | 0 | – | TN |
| 107 | G4 | F | 22 | — | — | 30 | – | TN |
| 108 | G4 | F | 33 | — | — | 70 | – | TN |
| 109 | G4 | F | 37 | — | — | 35.8 | – | TN |
| 110 | G4 | F | 33 | — | — | 61.5 | – | TN |
| 111 | G4 | F | 32 | — | — | 0 | – | TN |
| 112 | G4 | M | 42 | — | — | 5.1 | – | TN |
| 113 | G4 | M | 30 | — | — | 10.9 | – | TN |
| 114 | G4 | M | 38 | — | — | 1.7 | – | TN |
| 115 | G4 | F | 32 | — | — | 32.6 | – | TN |
| 116 | G4 | M | 37 | — | — | 7.2 | – | TN |
| 117 | G4 | M | 45 | — | — | 0 | – | TN |
| 118 | G4 | M | 49 | — | — | 5 | – | TN |
| 119 | G4 | M | 31 | — | — | 178 | – | TN |
| 120 | G4 | F | 51 | — | — | 224 | – | FP |
| 121 | G4 | M | 31 | — | — | 60 | – | TN |
| 122 | G4 | M | 53 | — | — | 72 | – | TN |
| 123 | G4 | F | 50 | — | — | 160 | – | TN |
| 124 | G4 | F | 41 | — | — | 57 | – | TN |
| 125 | G4 | F | 54 | — | — | 1.5 | – | TN |
| 126 | G4 | M | 60 | — | — | 43.7 | – | TN |
| 127 | G4 | M | 48 | — | — | 12 | – | TN |
| 128 | G4 | M | 47 | — | — | 19.8 | – | TN |
| 129 | G4 | M | 39 | — | — | 51 | – | TN |
| 130 | G4 | M | 55 | — | — | 67 | – | TN |
| 131 | G4 | M | 57 | — | — | 27 | – | TN |
| 132 | G4 | F | 38 | — | — | 34.9 | – | TN |
| 133 | G4 | F | 35 | — | — | 0 | – | TN |
| 134 | G4 | M | 39 | — | — | 0 | – | TN |
| 135 | G4 | F | 28 | — | — | 1.2 | – | TN |
| 136 | G4 | M | 27 | — | — | 3.5 | – | TN |
| 137 | G4 | F | 31 | — | — | 7.8 | – | TN |
| 138 | G4 | M | 28 | — | — | 24 | – | TN |
| 139 | G4 | F | 31 | — | — | 191.5 | – | FP |
| 140 | G4 | M | 39 | — | — | 0 | – | TN |
| 141 | G4 | M | 40 | — | — | 0.7 | – | TN |
| 142 | G4 | M | 25 | — | — | 0 | – | TN |

Note:
TP: True Positive, FP: False Positive, TN: True Negative, and FN: False Negative.

Table 4 shows comparative diagnostic results of 30 candidates who were recommended to do CT-Scan by the physicians due to their blood tests and physical symptoms. It should be noted that positive, suspicious and negative ranges may include current peak ranges higher than about 230 µA, a range of about 190-230 µA, and ranges lower than about 190 µA, respectively.

TABLE 4

Comparative diagnostic results of 30 candidates who were recommended to do CT-Scan by the physicians.

| ID | Gender | Age | Time of infection | Time of test | current peak (I) (µA) | CT-Scan diagnosis | Present diagnosis vs. CT-scan as a gold standard |
|---|---|---|---|---|---|---|---|
| 1 | F | 40 | Apr. 19, 2020 | 5$^{th}$ days after appearance of symptoms | 370.7 | + | TP |
| 2 | M | 48 | Apr. 20, 2020 | 4$^{th}$ days after appearance of symptoms | 339.8 | + | TP |
| 3 | M | 57 | Apr. 19, 2020 | 7$^{th}$ days after appearance of symptoms | 0 | – | TN |

TABLE 4-continued

Comparative diagnostic results of 30 candidates who were recommended to do CT-Scan by the physicians.

| ID | Gender | Age | Time of infection | Time of test | current peak (I) (µA) | CT-Scan diagnosis | Present diagnosis vs. CT-scan as a gold standard |
|---|---|---|---|---|---|---|---|
| 4 | F | 45 | Apr. 23, 2020 | $3^{th}$ days after appearance of symptoms | 520.9 | + | TP |
| 5 | F | 40 | Apr. 18, 2020 | $7^{th}$ days after appearance of symptoms | 5 | − | TN |
| 6 | M | 47 | Apr. 21, 2020 | $5^{th}$ days after appearance of symptoms | 43.2 | − | TN |
| 7 | M | 43 | Apr. 22, 2020 | $4^{th}$ days after appearance of symptoms | 11.7 | − | TN |
| 8 | M | 51 | Apr. 16, 2020 | $8^{th}$ days after appearance of symptoms | 784.09 | + | TP |
| 9 | M | 53 | Apr. 18, 2020 | $5^{th}$ days after appearance of symptoms | 3.2 | − | TN |
| 10 | F | 38 | Apr. 18, 2020 | $7^{th}$ days after appearance of symptoms | 193.7 | − | FP |
| 11 | M | 37 | Apr. 21, 2020 | $4^{th}$ days after appearance of symptoms | 4.3 | − | TN |
| 12 | F | 41 | Apr. 22, 2020 | $4^{th}$ days after appearance of symptoms | 0 | − | TN |
| 13 | F | 40 | Apr. 21, 2020 | $3^{th}$ days after appearance of symptoms | 270.1 | + | TP |
| 14 | M | 42 | Apr. 21, 2020 | $3^{th}$ days after appearance of symptoms | 356.4 | + | TP |
| 15 | M | 45 | Apr. 22, 2020 | $4^{th}$ days after appearance of symptoms | 412.6 | + | TP |
| 16 | M | 46 | Apr. 18, 2020 | $5^{th}$ days after appearance of symptoms | 47 | − | TN |
| 17 | F | 57 | Apr. 20, 2020 | $5^{th}$ days after appearance of symptoms | 185.4 | + | FN |
| 18 | M | 48 | Apr. 21, 2020 | $5^{th}$ days after appearance of symptoms | 11 | − | TN |
| 19 | M | 38 | Apr. 18, 2020 | $7^{th}$ days after appearance of symptoms | 294.2 | + | TP |
| 20 | M | 37 | Apr. 20, 2020 | $4^{th}$ days after appearance of symptoms | 40.2 | − | TN |
| 21 | F | 49 | Apr. 19, 2020 | $5^{th}$ days after appearance of symptoms | 0 | − | TN |
| 22 | F | 41 | Apr. 21, 2020 | $5^{th}$ days after appearance of symptoms | 27.9 | − | TN |
| 23 | M | 42 | Apr. 21, 2020 | $4^{th}$ days after appearance of symptoms | 506.7 | + | TP |
| 24 | M | 47 | Apr. 20, 2020 | $4^{th}$ days after appearance of symptoms | 0 | − | TN |
| 25 | M | 58 | Apr. 19, 2020 | $7^{th}$ days after appearance of symptoms | 8.3 | − | TN |
| 26 | F | 58 | Apr. 22, 2020 | $4^{th}$ days after appearance of symptoms | 400 | + | TP |
| 27 | M | 50 | Apr. 20, 2020 | $4^{th}$ days after appearance of symptoms | 468 | + | TP |
| 28 | M | 43 | Apr. 20, 2020 | $4^{th}$ days after appearance of symptoms | 388 | + | TP |
| 29 | F | 44 | Apr. 19, 2020 | $5^{th}$ days after appearance of symptoms | 17.8 | − | TN |
| 30 | F | 51 | Apr. 21, 2020 | $3^{th}$ days after appearance of symptoms | 9 | − | TN |

Note:
TP: True Positive, FP: False Positive, TN: True Negative, and FN: False Negative.

It may be resulted that the present exemplary probe, system, and method disclosed herein may be used as a power full assistant approach in fast screening of patients who need further medical examination during COVID-19 pandemic and may be used to reduce the number of cases that must be undergone CT-Scan for COVID-19 diagnosis.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A system for diagnosing COVID-19 infection, comprising:
    an electrochemical probe comprising three needle-shaped electrodes, the three needle-shaped electrodes configured to be inserted into a sputum sample;
    an electrochemical stimulator-analyzer electrically connected to the electrochemical probe; and
    a processing unit electrically connected to the electrochemical stimulator-analyzer, the processing unit comprising:
        a memory having processor-readable instructions stored therein; and
        a processor configured to access the memory and execute the processor-readable instructions, which, when executed by the processor configures the processor to perform a method, the method comprising:
            applying, utilizing the electrochemical stimulator-analyzer, a sweeping range of electrical potentials to the electrochemical probe;
            measuring, utilizing the electrochemical stimulator-analyzer, a set of electrical currents generated between a working electrode and a counter electrode of the three needle-shaped electrodes versus the applied sweeping range of electrical potential;
            receiving the set of electrical currents from the electrochemical stimulator-analyzer;
            measuring a level of reactive oxygen species (ROS) in the sputum sample by measuring a current peak of the set of electrical currents; and
            detecting a COVID-19 infection status based on the measured level of ROS, comprising:
                detecting a COVID-19 infection responsive to the measured current peak being in a first range of current peaks; and
                detecting a COVID-19 non-infection responsive to the measured current peak being in a second range of current peaks.

2. The system of claim 1, wherein applying the sweeping range of electrical potentials to the electrochemical probe comprises applying a sweeping range of electrical potentials from −0.8 V to +0.8 V with a scan rate of 100 mVs$^{-1}$ to the electrochemical probe.

3. The system of claim 1, wherein the first range of current peaks comprises a range of current peaks being more than 230 μA.

4. The system of claim 3, wherein the second range of current peaks comprises a range of current peaks being less than 190 μA.

5. The system of claim 1, wherein detecting the COVID-19 infection status further comprises detecting a suspicious condition of COVID-19 infection responsive to the measured current peak being in a third range of current peaks between the first range of current peaks and the second range of current peaks,
    wherein the suspicious condition of COVID-19 infection comprises an indication that there is no definite determination regarding COVID-19 infection of the person.

6. The system of claim 5, wherein the third range of current peaks comprises a range of current peaks between 190 μA and 230 μA.

7. The system of claim 1, wherein the method further comprises generating a calibration data set, comprising:
    generating the first range of current peaks by measuring a first set of ROS values in a respective first set of sputum samples acquired from a plurality of persons infected with COVID-19 virus; and
    generating the second range of current peaks by measuring a second set of ROS values in a respective second set of sputum samples acquired from a plurality of persons not infected with COVID-19 virus.

8. The system of claim 7, wherein detecting the COVID-19 infection status further comprises comparing the measured level of ROS with the ROS values in the calibration data set.

9. The system of claim 1, wherein the electrochemical probe comprises a sensing head comprising the three needle-shaped electrodes located at one end of the sensing head, each of the three needle-shaped electrodes comprises:
    a steel needle comprising a conical tip; and
    an array of multi-walled carbon nanotubes (MWCNTs) grown on the conical tip,
    wherein the three needle-shaped electrodes are attached at the one end of the sensing head with a distance between 1 mm and 5 mm between each two respective needle-shaped electrodes placed next to each other.

* * * * *